US010088473B2

(12) United States Patent
Lim et al.

(10) Patent No.: US 10,088,473 B2
(45) Date of Patent: Oct. 2, 2018

(54) BIO MARKER DETECTION DEVICE, ELECTRONIC DEVICE, AND METHOD FOR GENERATING HEALTH INFORMATION

(71) Applicant: Samsung Electronics Co., Ltd., Suwon-si, Gyeonggi-do (KR)

(72) Inventors: Jong-Min Lim, Suwon-si (KR); Jeong-Gun Lee, Seoul (KR); Joo-Won Rhee, Seongnam-si (KR); Jee-Yeon Kim, Seoul (KR); Sang-Hyun Baek, Hwaseong-si (KR); Seo-Young Yoon, Suwon-si (KR); Hyun-Joo Jung, Seoul (KR); Jae-Geol Cho, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 55 days.

(21) Appl. No.: 15/227,346

(22) Filed: Aug. 3, 2016

(65) Prior Publication Data

US 2017/0039441 A1 Feb. 9, 2017

(30) Foreign Application Priority Data

Aug. 3, 2015 (KR) ........................ 10-2015-0109613

(51) Int. Cl.
*G06K 9/00* (2006.01)
*G01N 33/50* (2006.01)
*G01N 21/78* (2006.01)
*G06F 19/00* (2018.01)
*G01N 21/77* (2006.01)

(52) U.S. Cl.
CPC ......... *G01N 33/5091* (2013.01); *G01N 21/78* (2013.01); *G06F 19/30* (2013.01); *G01N 2021/7759* (2013.01)

(58) Field of Classification Search
None
See application file for complete search history.

(56) References Cited

U.S. PATENT DOCUMENTS 8,446,463 B2 * 5/2013 Fleming ............. G01N 21/8483
348/61
9,241,663 B2 * 1/2016 Jena ................... G01N 21/8483
(Continued)

OTHER PUBLICATIONS

Feng et al., "Immunochromatographic diagnostic test analysis using Google Glass", ACS Nano, 2014, 8 (3), 3069-3079, Feb. 27, 2014.*
(Continued)

*Primary Examiner* — Soo Park
(74) *Attorney, Agent, or Firm* — Jefferson IP Law, LLP

(57) ABSTRACT

A bio marker detection device and a method for detecting or generating a bio marker from a plurality of strip sensors are provided. The bio marker detection device includes a close-up lens for detecting an image for the plurality of strip sensors, a transparent frame surrounding the close-up lens to evenly pass light from an outside to the plurality of strip sensors, and a strip sensor holder inlet configured for combining the plurality of strip sensors with the bio marker detection device. The method includes detecting a plurality of bio markers from a plurality of sensors, generating user health information based on the detected plurality of detected bio markers, and displaying the generated user health information.

16 Claims, 23 Drawing Sheets

(56) References Cited

U.S. PATENT DOCUMENTS

| | | | |
|---|---|---|---|
| 9,386,221 B2 * | 7/2016 | Kauniskangas | H04N 17/002 |
| 9,404,737 B2 * | 8/2016 | Segale | G01N 21/6458 |
| 2010/0045789 A1 * | 2/2010 | Fleming | G01N 21/8483 |
| | | | 348/79 |
| 2013/0280698 A1 * | 10/2013 | Propper | G01N 33/5302 |
| | | | 435/5 |
| 2014/0213468 A1 | 7/2014 | Ehrenkranz et al. | |
| 2015/0036875 A1 * | 2/2015 | Savransky | G06K 9/00671 |
| | | | 382/103 |

OTHER PUBLICATIONS

Mudanyali et al., "Integrated rapid-diagnostic-test reader platform on a cellphone", Lab Chop, 2012, 12, 2678-2686.*
Vashist et al., "Cellphone-based devices for bioanalytical sciences", Anal Bioanal Chem (2014) 406: 3263-3277, Nov. 28, 2013.*

* cited by examiner

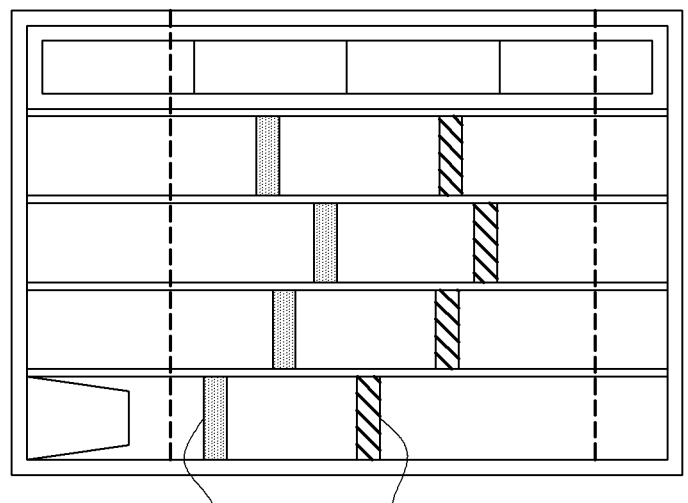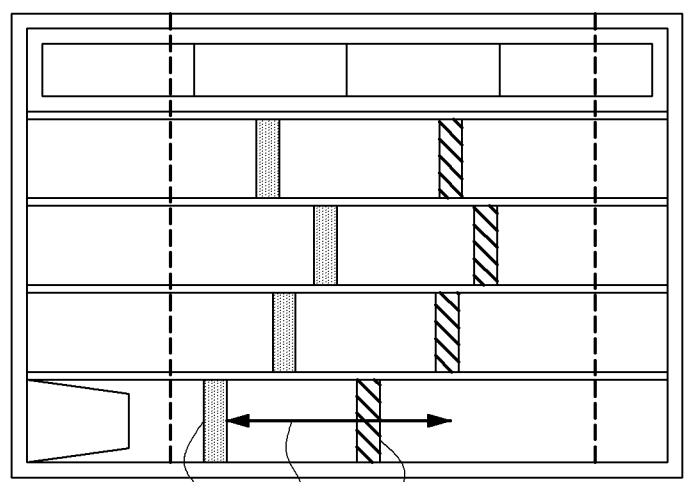
FIG.17

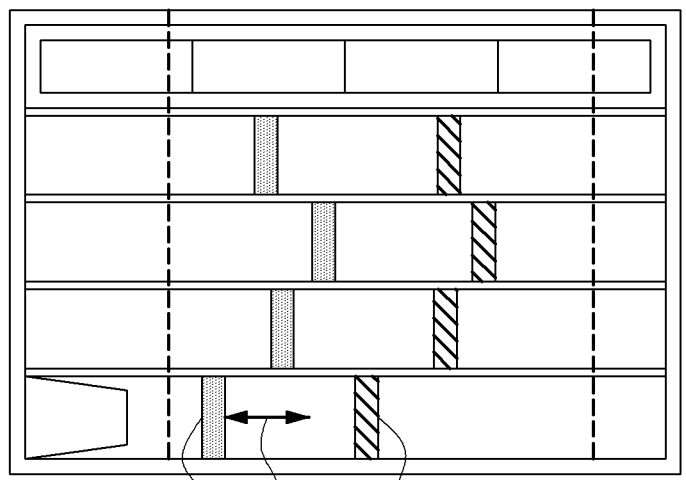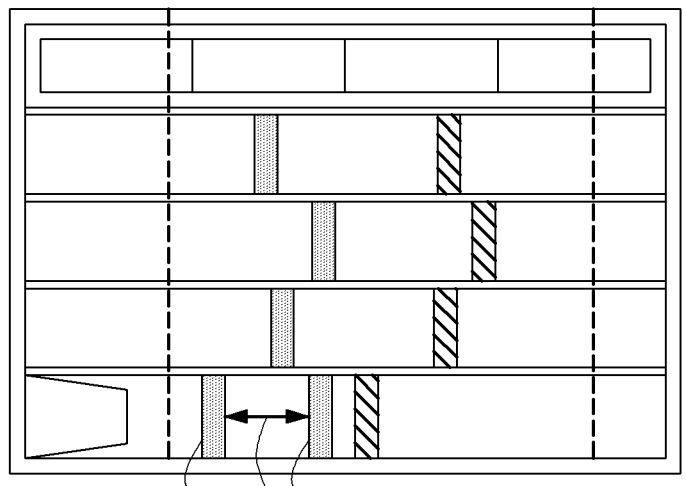
FIG.18

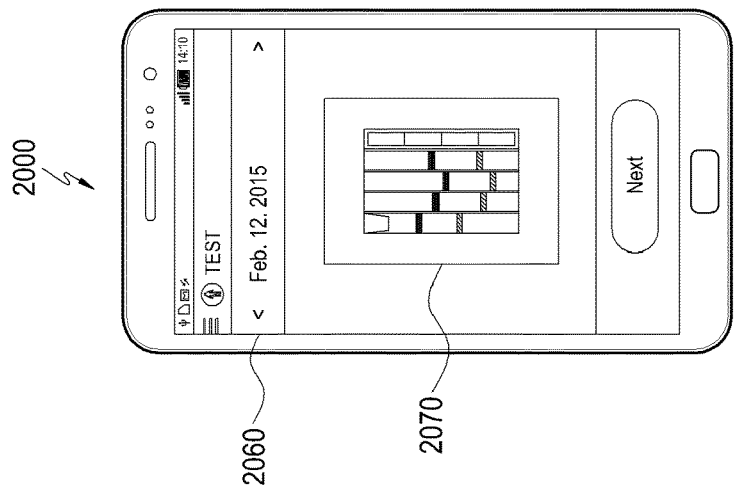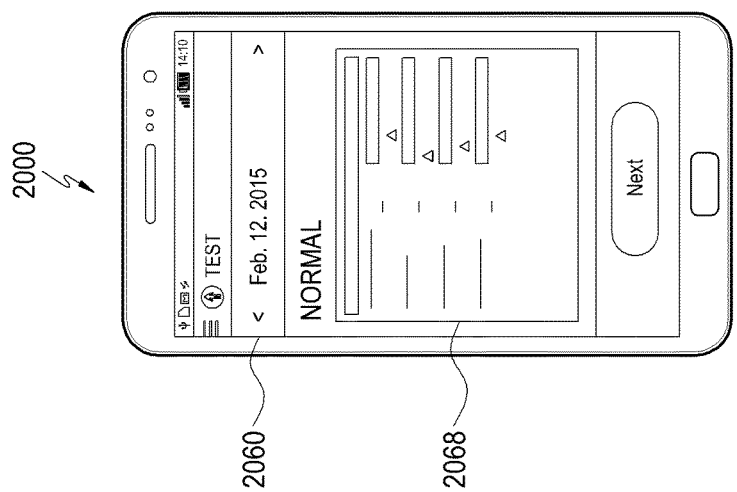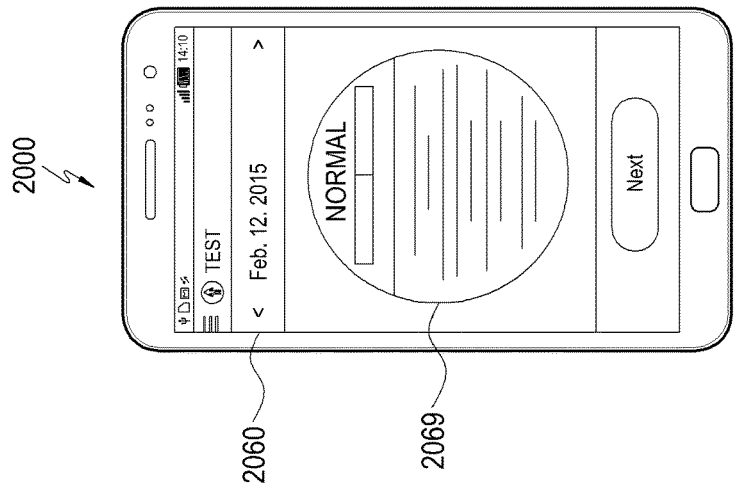

BIO MARKER DETECTION DEVICE, ELECTRONIC DEVICE, AND METHOD FOR GENERATING HEALTH INFORMATION

CROSS-REFERENCE TO RELATED APPLICATION(S)

This application claims the benefit under 35 U.S.C. § 119(a) of a Korean patent application filed on Aug. 3, 2015 in the Korean Intellectual Property Office and assigned Serial number 10-2015-0109613, the entire disclosure of which is hereby incorporated by reference.

TECHNICAL FIELD

The present disclosure relates to bio marker detection devices and electronic devices and methods for controlling the same. More particularly, the present disclosure relates to bio marker detection devices for detecting bio markers from plurality of strip sensors to generate health information, electronic devices for generating health information based on bio markers, and methods for controlling the bio marker detection devices and electronic devices.

BACKGROUND

Recently, smart device users are becoming more interested in their health information. They may access the Internet through the smart devices to obtain their health information or directly enter their health information to the smart devices to obtain diagnosis results. The users may extract their secretion or saliva and analyze the same through their smart devices and arbitrarily diagnose their health conditions by the result of the analysis.

For example, a smart device user may extract his secretion or saliva and put in a bio marker obtaining device with at least one strip sensor and obtain his or her bio markers through the smart device capable of detecting the respective concentrations of the bio markers.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide a bio marker detection device, electronic device, and method for obtaining bio markers from a plurality of strip sensors to generate the user's health information Conventional bio marker obtaining devices can obtain only one type of bio marker. The user makes an arbitrary diagnosis on his/her health condition based only on the concentration of the bio marker obtained by the strip sensor. As such, the conventional bio marker obtaining devices allow the user to measure concentration for only one bio marker, not plurality of bio markers, at each measurement of secretion or saliva, failing to give the user a comprehensive result on his/her health condition. Further, users who lack expertise in the detected bio marker may misdiagnose their health condition. Some conventional camera devices may simultaneously detect plurality of bio markers for plurality of strip sensors. However, the camera devices have a poor recognition ratio for strip sensors due to their physical limitations and fail to give exact or accurate bio markers.

According to various embodiments of the present disclosure, a bio marker detection device for detecting a bio marker from a plurality of strip sensors is provided. The bio marker detection device includes a close-up lens for detecting an image for the plurality of strip sensors, a transparent frame surrounding the close-up lens to evenly pass light from an external source to the plurality of strip sensors, and a strip sensor holder inlet configured for combining the plurality of strip sensors with the bio marker detection device.

According to various embodiments of the present disclosure, a method for generating health information from a plurality of strip sensors is provided. The method includes detecting a plurality of bio markers from a plurality of strip sensors, generating user health information based on the detected plurality of detected bio markers, and displaying the generated user health information.

According to various embodiments of the present disclosure, an electronic device generating health information from a plurality of strip sensors is provided. The electronic device includes a camera sensor for detecting a plurality of bio markers from a plurality of sensors, a processor configured to control for generating user health information based on the detected plurality of bio markers, and a display for displaying the generated user health information.

According to various embodiments of the present disclosure, the user may extract his secretion or saliva and simultaneously obtain the plurality of bio markers through the plurality of strip sensors. Thus, comprehensive diagnosis is possible. Further, the user may obtain his health condition information as generated by the electronic device and advice and analysis on the health condition information even without expertise in the bio markers obtained by the plurality of strip sensors. Further, the user may obtain more accurate and precise the plurality of bio markers contained in his secretion.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which:

FIGS. 17 and 18 are views illustrating a method for identifying a detection section according to various embodiments of the present disclosure;

FIGS. 20A, 20B, 20C, 21A, 21B, and 21C are views illustrating a method for generating health information according to various embodiments of the present disclosure.

Throughout the drawings, like reference numerals will be understood to refer to like parts, components, and structures.

DETAILED DESCRIPTION

Figure 1:
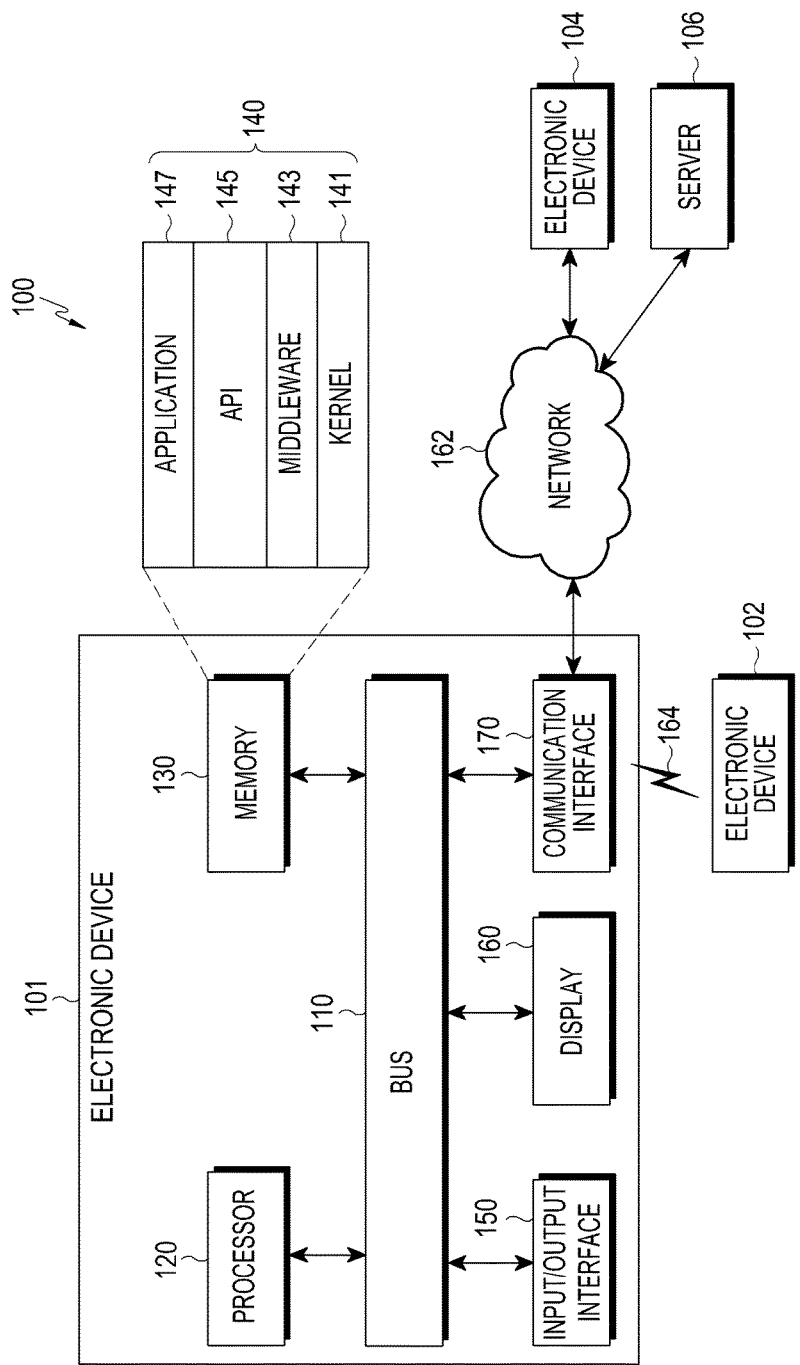
FIG. 1 is a block diagram illustrating an electronic device and a network according to various embodiments of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

As used herein, the terms "have," "may have," "include," or "may include" a feature (e.g., a number, function, operation, or a component such as a part) indicate the existence of the feature and do not exclude the existence of other features.

As used herein, the terms "A or B," "at least one of A and/or B," or "one or more of A and/or B" may include all possible combinations of A and B. For example, "A or B," "at least one of A and B," "at least one of A or B" may indicate all of (1) including at least one A, (2) including at least one B, or (3) including at least one A and at least one B.

As used herein, the terms "first" and "second" may modify various components regardless of importance and/or order and are used to distinguish a component from another without limiting the components. For example, a first user device and a second user device may indicate different user devices from each other regardless of the order or importance of the devices. For example, a first component may be denoted a second component, and vice versa without departing from the scope of the present disclosure.

It will be understood that when an element (e.g., a first element) is referred to as being (operatively or communicatively) "coupled with/to," or "connected with/to" another element (e.g., a second element), it can be coupled or connected with/to the other element directly or via a third element. In contrast, it will be understood that when an element (e.g., a first element) is referred to as being "directly coupled with/to" or "directly connected with/to" another element (e.g., a second element), no other element (e.g., a third element) intervenes between the element and the other element.

As used herein, the terms "configured (or set) to" may be interchangeably used with the terms "suitable for," "having the capacity to," "designed to," "adapted to," "made to," or "capable of" depending on circumstances. The term "configured (or set) to" does not essentially mean "specifically designed in hardware to." Rather, the term "configured to" may mean that a device can perform an operation together with another device or parts. For example, the term "processor configured (or set) to perform A, B, and C" may mean a generic-purpose processor (e.g., a central processing unit (CPU) or application processor (AP)) that may perform the operations by executing one or more software programs stored in a memory device or a dedicated processor (e.g., an embedded processor) for performing the operations.

The terms as used herein are provided merely to describe some embodiments thereof, but not to limit the scope of other embodiments of the present disclosure. It is to be understood that the singular forms "a," "an," and "the" include plural references unless the context clearly dictates otherwise. The terms including technical and scientific terms used herein have the same meaning as commonly understood by one of ordinary skill in the art to which the embodiments of the present disclosure belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some cases, the terms defined herein may be interpreted to exclude embodiments of the present disclosure.

For example, examples of the electronic device according to embodiments of the present disclosure may include at least one of a smartphone, a tablet personal computer (PC), a mobile phone, a video phone, an e-book reader, a desktop PC, a laptop computer, a netbook computer, a workstation, a personal digital assistant (PDA), a portable multimedia player (PMP), an MP3 player, a mobile medical device, a camera, or a wearable device. According to an embodiment of the present disclosure, the wearable device may include at least one of an accessory-type device (e.g., a watch, a ring, a bracelet, an anklet, a necklace, glasses, contact lenses, or a head-mounted device (HMD)), a fabric- or clothes-integrated device (e.g., electronic clothes), a body attaching-type device (e.g., a skin pad or tattoo), or a body implantable device (e.g., an implantable circuit).

According to an embodiment of the present disclosure, the electronic device may be a home appliance. Examples of the home appliance may include at least one of a television, a digital versatile disc (DVD) player, an audio player, a refrigerator, an air conditioner, a cleaner, an oven, a microwave oven, a washer, a drier, an air cleaner, a set-top box, a home automation control panel, a security control panel, a TV box (e.g., Samsung HomeSync™, Apple TV™, or Google TV™), a gaming console (Xbox™, PlayStation™), an electronic dictionary, an electronic key, a camcorder, or an electronic picture frame.

According to an embodiment of the present disclosure, examples of the electronic device may include at least one of various medical devices (e.g., diverse portable medical measuring devices (a blood sugar measuring device, a heartbeat measuring device, or a body temperature measuring device), a magnetic resource angiography (MRA) device, a magnetic resource imaging (MRI) device, a computed tomography (CT) device, an imaging device, or an ultrasonic device), a navigation device, a global navigation satellite system (GNSS) receiver or a global positioning satellite (GPS) receiver, an event data recorder (EDR), a flight data recorder (FDR), an automotive infotainment device, an sailing electronic device (e.g., a sailing navigation device or a gyro compass), avionics, security devices, vehicular head units, industrial or home robots, automatic teller's machines (ATMs), point of sales (POS) devices, or Internet of Things devices (e.g., a bulb, various sensors, an electric or gas meter, a sprinkler, a fire alarm, a thermostat, a street light, a toaster, fitness equipment, a hot water tank, a heater, or a boiler).

According to various embodiments of the disclosure, examples of the electronic device may at least one of part of a piece of furniture or building/structure, an electronic board, an electronic signature receiving device, a projector, or various measurement devices (e.g., devices for measuring water, electricity, gas, or electromagnetic waves). According to an embodiment of the present disclosure, the electronic device may be one or a combination of the above-listed devices. According to an embodiment of the present disclosure, the electronic device may be a flexible electronic device. The electronic device disclosed herein is not limited to the above-listed devices, and may include new electronic devices depending on the development of technology.

Hereinafter, electronic devices are described with reference to the accompanying drawings, according to various embodiments of the present disclosure. As used herein, the term "user" may denote a human or another device (e.g., an artificial intelligent electronic device) using the electronic device.

FIG. 1 is a block diagram illustrating an electronic device and a network according to various embodiments of the present disclosure.

Referring to FIG. 1, an electronic device 101 is included in a network environment 100. The electronic device 101 may include a bus 110, a processor 120, a memory 130, an input/output interface 150, a display 160, and a communication module or communication interface 170. In some embodiments, the electronic device 101 may exclude at least one of the components or may add another component.

The bus 110 may include a circuit for connecting the components 110 to 170 with one another and transferring communications (e.g., control messages and/or data) between the components.

The processing module or processor 120 may include one or more of a central processing unit (CPU), an application processor (AP), or a communication processor (CP). The processor 120 may perform control on at least one of the other components of the electronic device 101, and/or perform an operation or data processing relating to communication.

The memory 130 may include a volatile and/or non-volatile memory. For example, the memory 130 may store commands or data related to at least one other component of the electronic device 101. According to an embodiment of the present disclosure, the memory 130 may store software and/or a program 140. The program 140 may include, e.g., a kernel 141, middleware 143, an application programming interface (API) 145, and/or an application program (or "application") 147. At least a portion of the kernel 141, middleware 143, or API 145 may be denoted an operating system (OS).

For example, the kernel 141 may control or manage system resources (e.g., the bus 110, processor 120, or a memory 130) used to perform operations or functions implemented in other programs (e.g., the middleware 143, API 145, or application program 147). The kernel 141 may provide an interface that allows the middleware 143, the API 145, or the application 147 to access the individual components of the electronic device 101 to control or manage the system resources.

The middleware 143 may function as a relay to allow the API 145 or the application 147 to communicate data with the kernel 141, for example.

Further, the middleware 143 may process one or more task requests received from the application program 147 in order of priority. For example, the middleware 143 may assign at least one of application programs 147 with priority of using system resources (e.g., the bus 110, processor 120, or memory 130) of at least one electronic device 101. For example, the middleware 143 may perform scheduling or load balancing on the one or more task requests by processing the one or more task requests according to the priority assigned to the at least one application program 147.

Referring to FIG. 1, the API 145 is an interface allowing the application 147 to control functions provided from the kernel 141 or the middleware 143. For example, the API 133 may include at least one interface or function (e.g., a command) for filing control, window control, image processing or text control.

The input/output interface 150 may serve as an interface that may, e.g., transfer commands or data input from a user or other external devices to other component(s) of the electronic device 101. Further, the input/output interface 150 may output commands or data received from other component(s) of the electronic device 101 to the user or the other external device.

The display 160 may include, e.g., a liquid crystal display (LCD), a light emitting diode (LED) display, an organic light emitting diode (OLED) display, or a microelectromechanical systems (MEMS) display, or an electronic paper display. The display 160 may display, e.g., various contents (e.g., text, images, videos, icons, or symbols) to the user. The display 160 may include a touchscreen and may receive, e.g., a touch, gesture, proximity or hovering input using an electronic pen or a body portion of the user.

For example, the communication module 170 may set up communication between the electronic device 101 and an external device (e.g., a first electronic device 102, a second electronic device 104, or a server 106). For example, the communication module 170 may be connected with the network 162 through wireless or wired communication to communicate with the external electronic device (e.g., the second external electronic device 104 or server 106).

The wireless communication may be a cellular communication protocol and may use at least one of, e.g., long-term evolution (LTE), LTE-advanced (LTE-A), code division plurality of access (CDMA), wideband CDMA (WCDMA), universal mobile telecommunications system (UMTS), wireless broadband (WiBro), or global system for mobile communications (GSM). Further, the wireless communication may include, e.g., short-range communication 164. The short-range communication 164 may include at least one of wireless fidelity (Wi-Fi), Bluetooth (BT), near-field communication (NFC), or global navigation satellite system (GNSS). The GNSS may include at least one of, e.g., global positioning system (GPS), global navigation satellite system (Glonass), Beidou navigation satellite system (hereinafter, "Beidou") or Galileo, or the European global satellite-based navigation system. Hereinafter, the terms "GPS" and the "GNSS" may be interchangeably used herein. The wired connection may include at least one of, e.g., universal serial bus (USB), high definition multimedia interface (HDMI), recommended standard (RS)-232, or plain old telephone service (POTS). The network 162 may include at least one of communication networks, e.g., a computer network (e.g., local area network (LAN) or wide area network (WAN)), Internet, or a telephone network.

The first and second external electronic devices 102 and 104 each may be a device of the same or a different type from the electronic device 101. According to an embodiment of the present disclosure, the server 106 may include a group of one or more servers. According to an embodiment of the present disclosure, all or some of operations executed on the electronic device 101 may be executed on another or plurality of other electronic devices (e.g., the electronic devices 102 and 104 or server 106). According to an embodiment of the present disclosure, when the electronic device 101 should perform some function or service automatically or at a request, the electronic device 101, instead of executing the function or service on its own or additionally, may request another device (e.g., electronic devices 102 and 104 or server 106) to perform at least some functions associated therewith. The other electronic device (e.g., electronic devices 102 and 104 or server 106) may execute the requested functions or additional functions and transfer a result of the execution to the electronic device 101. The electronic device 101 may provide a requested function or service by processing the received result as it is or additionally. To that end, a cloud computing, distributed computing, or client-server computing technique may be used, for example.

Figure 2:
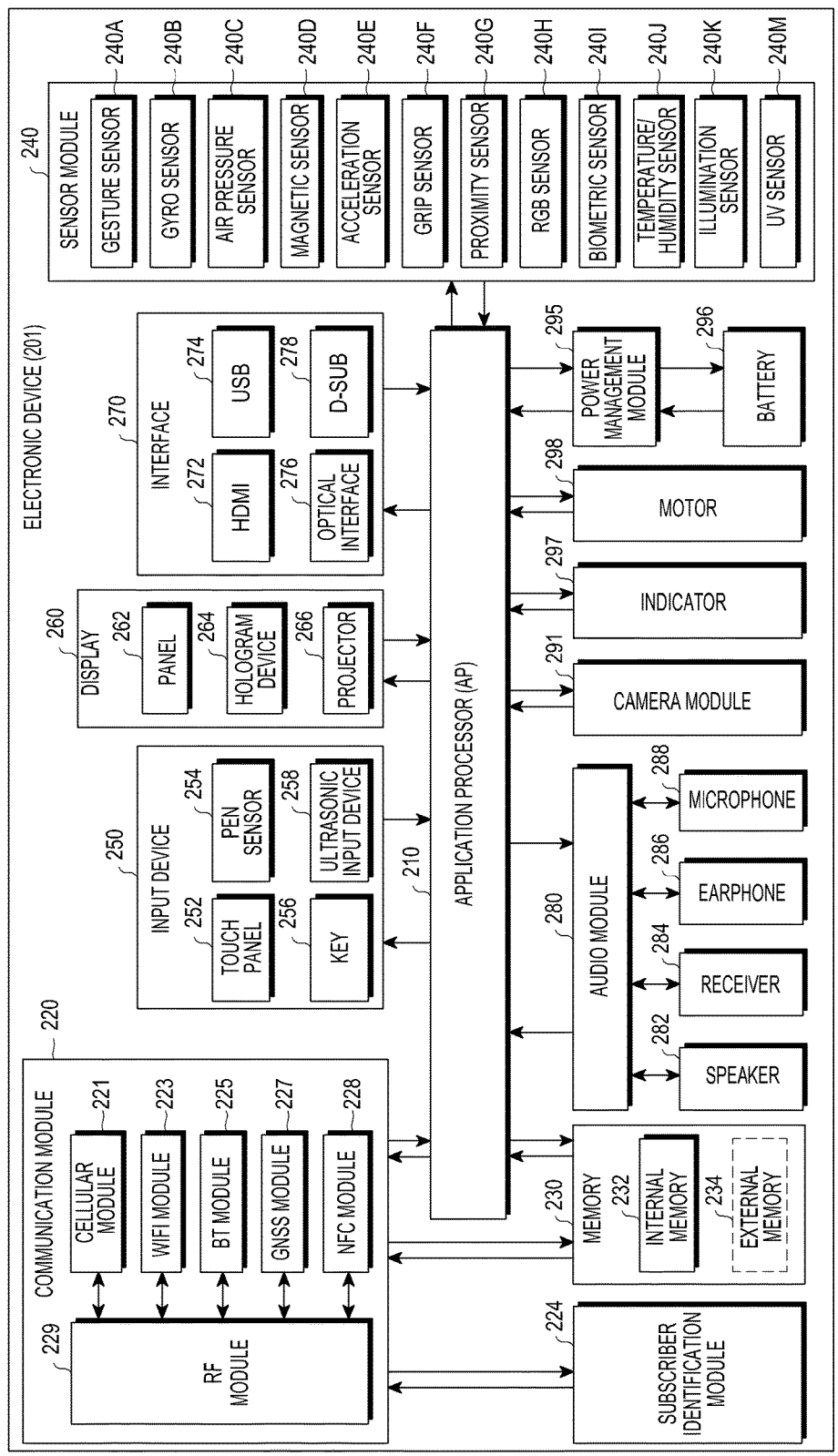
FIG. 2 is a block diagram illustrating an electronic device according to various embodiments of the present disclosure.

FIG. 2 is a block diagram illustrating an electronic device 201 according to various embodiments of the present disclosure.

Referring to FIG. 2, the electronic device 201 may include the whole or part of the configuration of, e.g., the electronic device 101 shown in FIG. 1. The electronic device 201 may include one or more processors (e.g., application processors (APs)) 210, a communication module 220, a subscriber identification module (SIM) 224, a memory 230, a sensor module 240, an input device 250, a display 260, an interface 270, an audio module 280, a camera module 291, a power management module 295, a battery 296, an indicator 297, and a motor 298.

The processor 210 may be configured to control a plurality of hardware and software components connected to the processor 210 by running, e.g., an operating system or application programs, and the processor 210 may process and compute various data. The processor 210 may be implemented in, e.g., a system on chip (SoC). According to an embodiment of the present disclosure, the processor 210 may further include a graphic processing unit (GPU) and/or an image signal processor. The processor 210 may include at least some (e.g., the cellular module 221) of the components shown in FIG. 2. The processor 210 may load a command or data received from at least one of other components (e.g., a non-volatile memory) on a volatile memory, process the command or data, and store various data in the non-volatile memory.

Referring to FIG. 2, the communication module 220 may have the same or similar configuration to the communication interface 170 of FIG. 1. The communication module 220 may include, e.g., a cellular module 221, a Wi-Fi module 223, a Bluetooth (BT) module 225, a GNSS module 227 (e.g., a GPS module, a Glonass module, a Beidou module, or a Galileo module), an NFC module 228, and a radio frequency (RF) module 229.

The cellular module 221 may provide voice call, video call, text, or Internet services through, e.g., a communication network. The cellular module 221 may perform identification or authentication on the electronic device 201 in the communication network using a subscriber identification module 224 (e.g., the SIM card). According to an embodiment of the present disclosure, the cellular module 221 may perform at least some of the functions providable by the processor 210. According to an embodiment of the present disclosure, the cellular module 221 may include a CP.

The Wi-Fi module 223, the Bluetooth module 225, the GNSS module 227, or the NFC module 228 may include a processor for, e.g., processing data communicated through the module. According to an embodiment of the present disclosure, at least some (e.g., two or more) of the cellular module 221, the Wi-Fi module 223, the Bluetooth module 225, the GNSS module 227, or the NFC module 228 may be included in a single integrated circuit (IC) or an IC package.

The RF module 229 may communicate data, e.g., communication signals (e.g., RF signals). The RF module 229 may include, e.g., a transceiver, a power amplifier module (PAM), a frequency filter, a low noise amplifier (LNA), or an antenna. According to an embodiment of the present disclosure, at least one of the cellular module 221, the Wi-Fi module 223, the Bluetooth module 225, the GNSS module 227, or the NFC module 228 may communicate RF signals through a separate RF module.

The subscription identification module 224 may include, e.g., a card including a subscriber identification module and/or an embedded SIM, and may contain unique identification information (e.g., an integrated circuit card identifier (ICCID) or subscriber information (e.g., an international mobile subscriber identity (IMSI)).

Referring to FIG. 2, the memory 230 (e.g., the memory 130) may include, e.g., an internal memory 232 or an external memory 234. The internal memory 232 may include at least one of, e.g., a volatile memory (e.g., a dynamic RAM (DRAM), a static RAM (SRAM), a synchronous dynamic RAM (SDRAM), etc.) or a non-volatile memory (e.g., a one-time programmable ROM (OTPROM), a programmable ROM (PROM), an erasable and programmable ROM (EPROM), an electrically erasable and programmable ROM (EEPROM), a mask ROM, a flash ROM, a flash memory (e.g., a NAND flash, or a NOR flash), a hard drive, or solid state drive (SSD).

The external memory 234 may include a flash drive, e.g., a compact flash (CF) memory, a secure digital (SD) memory, a micro-SD memory, a min-SD memory, an extreme digital (xD) memory, a multi-media card (MMC), or a memory Stick™. The external memory 234 may be functionally and/or physically connected with the electronic device 201 via various interfaces.

With reference to FIG. 2, the sensor module 240, for example, may measure a physical quantity or detect a motion state of the electronic device 201, and the sensor module 240 may convert the measured or detected information into an electrical signal. The sensor module 240 may include at least one of, e.g., a gesture sensor 240A, a gyro sensor 240B, an atmospheric pressure sensor or air pressure sensor 240C, a magnetic sensor 240D, an acceleration sensor 240E, a grip sensor 240F, a proximity sensor 240G, a color sensor 240H (e.g., an Red-Green-Blue (RGB) sensor, a bio or biometric sensor 240I, a temperature/humidity sensor 240J, an illumination sensor 240K, or an ultraviolet (UV) sensor 240M. Additionally or alternatively, the sensing module 240 may include, e.g., an E-nose sensor, an electromyography (EMG) sensor, an electroencephalogram (EEG) sensor, an electrocardiogram (ECG) sensor, an infrared (IR) sensor, an iris sensor, or a finger print sensor. The sensor module 240 may further include a control circuit for controlling at least one or more of the sensors included in the sensing module. According to an embodiment of the present disclosure, the electronic device 201 may further include a processor configured to control the sensor module 240 as part of the processor 210 or separately from the processor 210, and the electronic device 2701 may control the sensor module 240 while the processor 210 is in a sleep mode.

Referring to FIG. 2, the input unit 250 may include, e.g., a touch panel 252, a digital stylus or (digital) pen sensor 254, a key 256, or an ultrasonic input device 258. The touch panel 252 may use at least one of capacitive, resistive, infrared, or ultrasonic methods. The touch panel 252 may further include a control circuit. The touch panel 252 may further include a tactile layer and may provide a user with a tactile reaction.

The digital stylus or (digital) pen sensor 254 may include, e.g., a part of a touch panel or a separate sheet for recognition. The key 256 may include e.g., a physical button, optical key or key pad. The ultrasonic input device 258 may sense an ultrasonic wave generated from an input tool through a microphone (e.g., the microphone 288) to identify data corresponding to the sensed ultrasonic wave.

The display 260 (e.g., the display 160) may include a panel 262, a hologram device 264, or a projector 266. The panel 262 may have the same or similar configuration to the display 160 of FIG. 1. The panel 262 may be implemented to be flexible, transparent, or wearable. The panel 262 may also be incorporated with the touch panel 252 in a module. The hologram device 264 may make three dimensional (3D) images (holograms) in the air by using light interference. The projector 266 may display an image by projecting light onto a screen. The screen may be, for example, located inside or outside of the electronic device 201. In accordance with an embodiment, the display 260 may further include a control circuit to control the panel 262, the hologram device 264, or the projector 266.

The interface 270 may include e.g., a High Definition Multimedia Interface (HDMI) 272, a USB 274, an optical interface 276, or a D-subminiature (D-sub) 278. The interface 270 may be included in e.g., the communication interface 170 shown in FIG. 1. Additionally or alternatively, the interface 270 may include a mobile high-definition link (MHL) interface, a SD card/MMC interface, or IrDA standard interface.

Referring to FIG. 2, the audio module 280 may convert a sound into an electric signal or vice versa, for example. At least a part of the audio module 280 may be included in e.g., the input/output interface 150 as shown in FIG. 1. The audio module 280 may process sound information input or output through e.g., a speaker 282, a receiver 284, an earphone 286, or a microphone 288.

With reference to FIG. 2, the camera module 291, for example, may be a device for recording still images and videos, and may include, according to an embodiment of the present disclosure, one or more image sensors (e.g., front and back sensors), a lens, an Image signal processor (ISP), or a flash such as an LED or xenon lamp.

The power manager module 295 may manage power of the electronic device 201, for example. Although not shown, according to an embodiment of the present disclosure, the power manager module 295 may include a power management Integrated circuit (PMIC), a charger IC, or a battery or fuel gauge. The PMIC may have a wired and/or wireless recharging scheme. The wireless charging scheme may include e.g., a magnetic resonance scheme, a magnetic induction scheme, or an electromagnetic wave based scheme, and an additional circuit, such as a coil loop, a resonance circuit, a rectifier, or the like may be added for wireless charging. The battery gauge may measure an amount of remaining power of the battery 296, a voltage, a current, or a temperature while the battery 296 is being charged. The battery 296 may include, e.g., a rechargeable battery or a solar battery.

The indicator 297 may indicate a particular state of the electronic device 201 or a part (e.g., the processor 210) of the electronic device, including e.g., a booting state, a message state, or recharging state. The motor 298 may convert an electric signal to a mechanical vibration and may generate a vibrational or haptic effect. Although not shown, a processing unit for supporting mobile TV, such as a GPU may be included in the electronic device 201. The processing unit for supporting mobile TV may process media data conforming to a standard for Digital Multimedia Broadcasting (DMB), Digital Video Broadcasting (DVB), or mediaFlo™.

Each of the aforementioned components of the electronic device may include one or more parts, and a name of the part may vary with a type of the electronic device. The electronic device in accordance with various embodiments of the present disclosure may include at least one of the aforementioned components, omit some of them, or include other additional component(s). Some of the components may be combined into an entity, but the entity may perform the same functions as the components may do.

Figure 3:
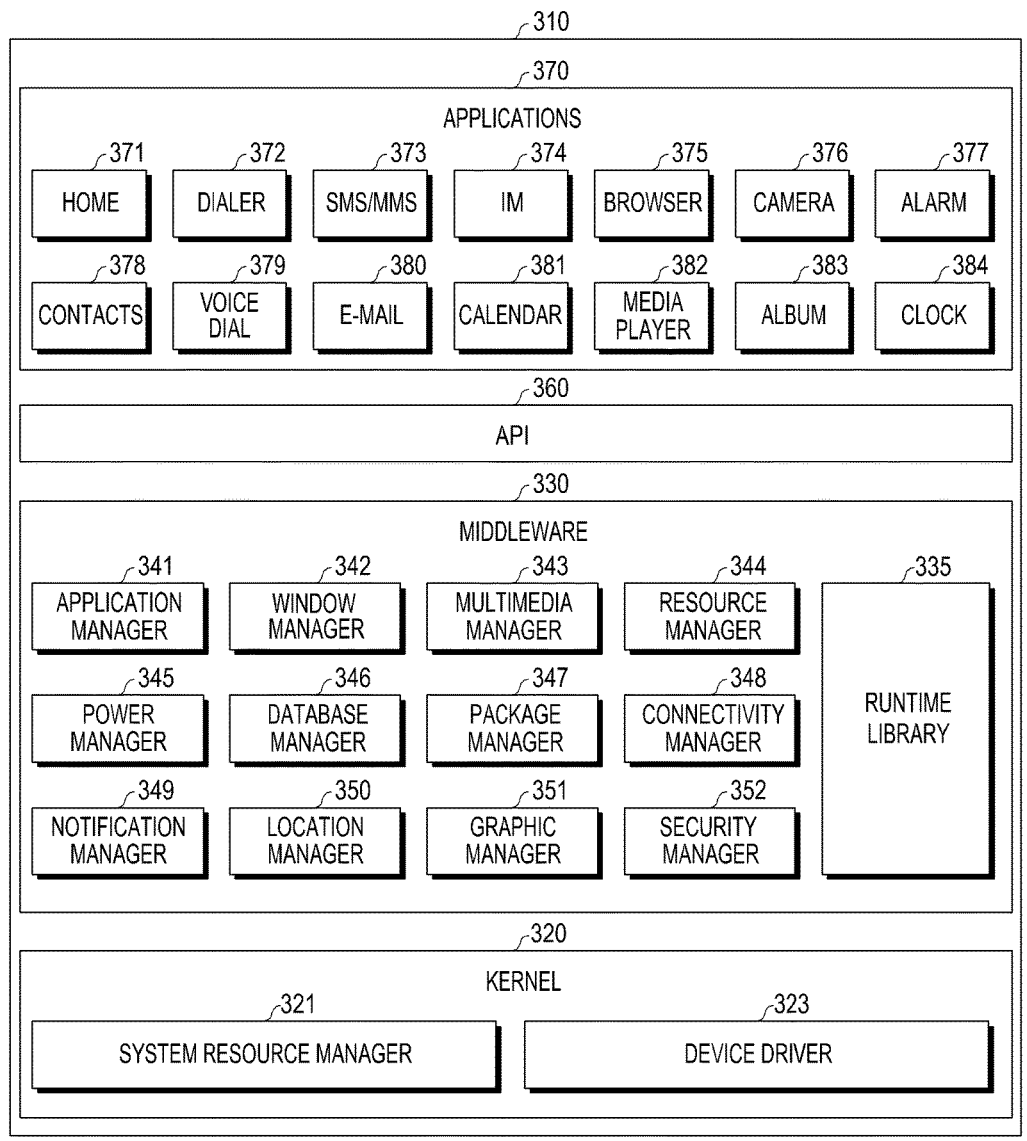
FIG. 3 is a block diagram illustrating a program module according to various embodiments of the present disclosure.

FIG. 3 is a block diagram illustrating a program module according to various embodiments of the present disclosure.

According to an embodiment of the present disclosure, the program module 310 (e.g., the program 140, shown in FIG. 1) may include an operating system (OS) controlling resources related to the electronic device (e.g., the electronic device 101) and/or various applications (e.g., the application processor 147, shown in FIG. 1) driven on the operating system. The operating system may include, e.g., Android®, iOS®, Windows®, Symbian®, Tizen®, or Bada®.

The program 310 may include, e.g., a kernel 320, middleware 330, an application programming interface (API) 360, and/or an application 370. At least a part of the program module 310 may be preloaded on the electronic device or may be downloaded from an external electronic device (e.g., the electronic devices 102 and 104 or server 106, shown in FIG. 1).

Referring to FIG. 3, the kernel 320 (e.g., the kernel 141) may include, e.g., a system resource manager 321 and/or a device driver 323. The system resource manager 321 may perform control, allocation, or recovery of system resources. According to an embodiment of the present disclosure, the system resource manager 321 may include a process managing unit, a memory managing unit, or a file system managing unit. The device driver 323 may include, e.g., a display driver, a camera driver, a Bluetooth driver, a shared memory driver, a USB driver, a keypad driver, a Wi-Fi driver, an audio driver, or an inter-process communication (IPC) driver.

Referring to FIG. 3, the middleware 330 may provide various functions to the application 370 through the API 360 so that the application 370 may efficiently use limited system resources in the electronic device or provide functions jointly required by applications 370. According to an embodiment of the present disclosure, the middleware 330 (e.g., the middleware 143 shown in FIG. 1) may include at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, or a security manager 352.

The runtime library 335 may include a library module used by a compiler in order to add a new function through a programming language while, e.g., the application 370 is being executed. The runtime library 335 may perform input/output management, memory management, or operation on arithmetic functions.

The application manager 341 may manage the life cycle of at least one application of, e.g., the applications 370. The window manager 342 may manage GUI resources used on the screen. The multimedia manager 343 may grasp formats necessary to play various media files and use a codec appropriate for a format to perform encoding or decoding on media files. The resource manager 344 may manage resources, such as source code of at least one of the applications 370, memory or storage space.

The power manager 345 may operate together with, e.g., a basic input/output system (BIOS) to manage battery or power and provide power information necessary for operating the electronic device. The database manager 346 may generate, search, or vary a database to be used in at least one of the applications 370. The package manager 347 may manage installation or update of an application that is distributed in the form of a package file.

Referring to FIG. 3, the connectivity manager 348 may manage wireless connectivity, such as, e.g., Wi-Fi or Bluetooth. The notification manager 349 may display or notify an event, such as a coming message, appointment, or proximity notification, of the user without interfering with the user. The location manager 350 may manage locational information on the electronic device. The graphic manager 351 may manage graphic effects to be offered to the user and their related user interface. The security manager 352 may provide various security functions necessary for system security or user authentication. According to an embodiment of the present disclosure, when the electronic device (e.g., the electronic device 101) has telephony capability, the middleware 330 may further include a telephony manager for managing voice call or video call functions of the electronic device.

The middleware 330 may include a middleware module forming a combination of various functions of the above-described components. The middleware 330 may provide a specified module per type of the operating system in order to provide a differentiated function. Further, the middleware 330 may dynamically omit some existing components or add new components.

With reference to FIG. 3, the API 360 (e.g., the API 145 shown in FIG. 1) may be a set of, e.g., API programming functions and may have different configurations depending on operating systems. For example, in the case of Android® or iOS®, one API set may be provided per platform, and in the case of Tizen®, two or more API sets may be offered per platform.

The application 370 (e.g., the application processor 147) may include one or more applications that may provide functions such as, e.g., a home 371, a dialer 372, a short message service (SMS)/multimedia messaging service (MMS) 373, an instant message (IM) 374, a browser 375, a camera 376, an alarm 377, a contact or contacts 378, a voice dial 379, an e-mail 380, a calendar 381, a media player 382, an album 383, a watch or clock 384, or other applications (not shown) including a health-care (e.g., measuring the degree of workout or blood sugar), or provision of environmental information (e.g., provision of air pressure, moisture, or temperature information).

According to an embodiment of the present disclosure, with reference to FIG. 3, the application 370 may include an application (hereinafter, "information exchanging application" for convenience) supporting information exchange between the electronic device (e.g., the electronic device 101) and an external electronic device (e.g., the electronic devices 102 and 104). Examples of the information exchange application may include, but is not limited to, a notification relay application for transferring specific information to the external electronic device, or a device management application for managing the external electronic device.

For example, the notification relay application may include a function for relaying notification information generated from other applications of the electronic device (e.g., the SMS/MMS application, email application, health-care application, or environmental information application) to the external electronic device (e.g., the electronic devices 102 and 104). Further, the notification relay application may receive notification information from, e.g., the external electronic device and may provide the received notification information to the user.

The device management application may perform at least some functions of the external electronic device (e.g., the electronic device 102 or 104) communicating with the electronic device (for example, turning on/off the external electronic device (or some components of the external electronic device) or control of brightness (or resolution) of the display), and the device management application may manage (e.g., install, delete, or update) an application operating in the external electronic device or a service (e.g., call service or message service) provided from the external electronic device.

According to an embodiment of the present disclosure, the application 370 may include an application (e.g., a health-care application of a mobile medical device) designated according to an attribute of the external electronic device (e.g., the electronic devices 102 and 104, shown in FIG. 1). According to an embodiment of the present disclosure, the application 370 may include an application received from the external electronic device (e.g., the server 106 or electronic devices 102 and 104, shown in FIG. 1). According to an embodiment of the present disclosure, the application 370 may include a preloaded application or a third party application downloadable from a server. The names of the components of the program module 310 according to the shown embodiment may be varied depending on the type of operating system.

According to an embodiment of the present disclosure, with reference to FIG. 3, at least a part of the program module 310 may be implemented in software, firmware, hardware, or in a combination of two or more thereof. At least a part of the programming module 310 may be implemented (e.g., executed) by e.g., a processor (e.g., the processor 210, shown in FIG. 2). At least a part of the program module 310 may include e.g., a module, program, routine, set of instructions, process, or the like for performing one or more functions.

Figure 4:
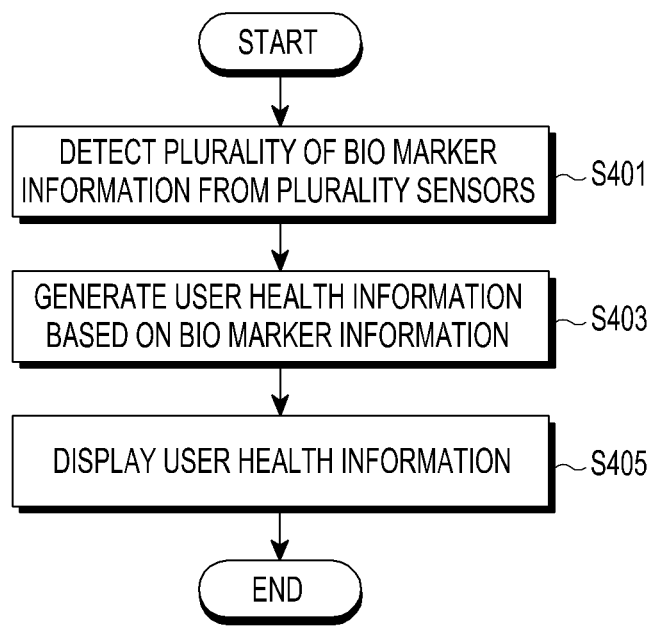
FIG. 4 is a flowchart illustrating a method for generating health information by an electronic device according to various embodiments of the present disclosure.

FIG. 4 is a flowchart illustrating a method for generating health information by an electronic device according to various embodiments of the present disclosure.

Referring to FIG. 4, in operation S401, the electronic device (e.g., the electronic device 101) may detect a plurality of bio markers from a plurality of sensors.

The plurality of sensors may include at least two strip sensors. Each of the plurality of strip sensors may include a determination section (or control section, control line) and a detection section (or test section, test line). Each of the plurality of strip sensors may be configured to include a plurality of bio marker that is a basis for generating the user's particular health information from the user's secretion. For example, each of the plurality of strip sensors may be configured to include, e.g. information on the content of cortisol, dehydroepiandrosterone sulfate (DHEA-s), vitamin D, adrenaline, and sodium which are bases for generating melancholy information (an example of the user's health information) from the user's secretion. The electronic device 101 (shown in FIG. 1) may detect the plurality of bio marker included in the plurality of sensors through a sensor module (e.g., the sensor module 240). For example, the electronic device 101 may detect the bio marker included in the plurality of sensors through a camera module (e.g., the camera module 291).

Referring to FIG. 3, in operation S403, the electronic device 101 (shown in FIG. 1) may generate the user's health information based on the plurality of bio marker detected from the plurality of sensors. For example, the electronic device 101 may generate information indicating that the user's health is in a normal condition or risky condition based on the plurality of detected bio marker. For example, the information on the user's health condition may include the degree of risk on the user's particular disease. For example, the user's health information may include advice (or map) information on the user's life style.

In operation S405, the electronic device 101 may display the generated user health information through a display (e.g., the display 160).

Figure 5A:
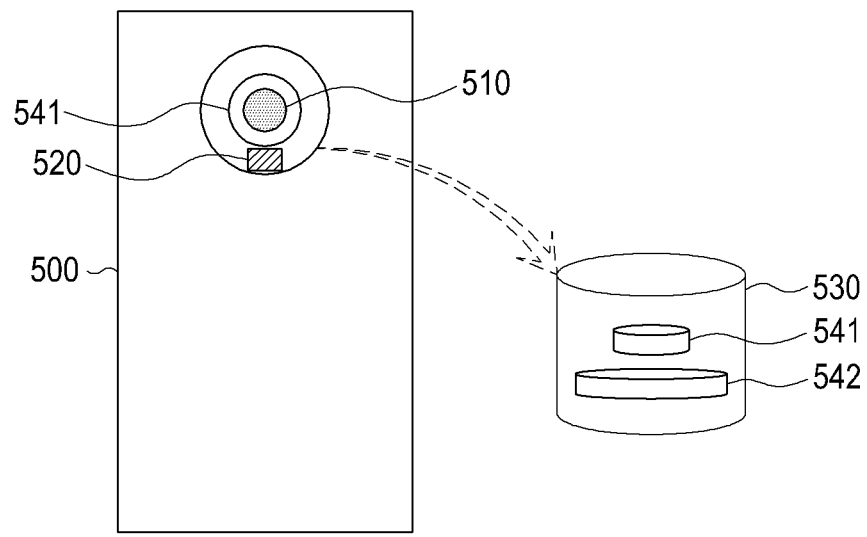
FIGS. 5A and 5B are views illustrating a health information detection device and electronic device according to various embodiments of the present disclosure.
Figure 5B:
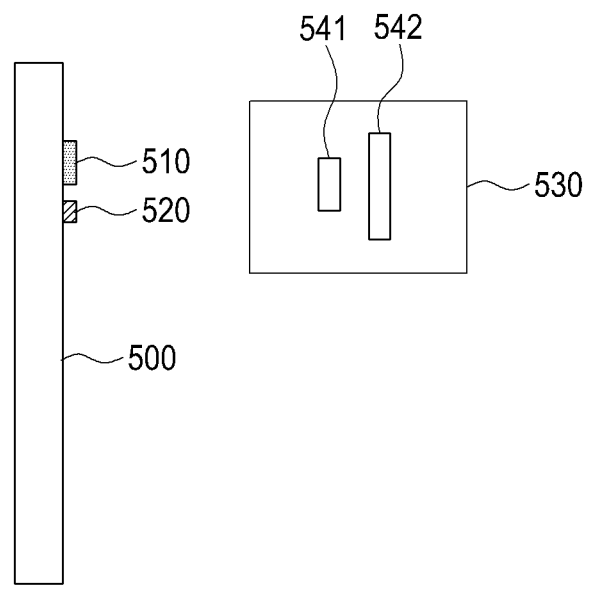

FIGS. 5A and 5B are views illustrating a health information detection device and electronic device according to various embodiments of the present disclosure.

FIG. 5A shows the rear surface of the electronic device 500. Referring to FIGS. 5A and 5B, a rear camera 510 and flash 520 may be provided in the rear surface of the electronic device 500. According to an embodiment of the present disclosure, the health information detection device may include a plurality of close-up lenses 541 and 542 and a transparent frame 530 surrounding the plurality of close-up lenses 541 and 542. According to an embodiment of the present disclosure, when the health information detection device is combined with the electronic device 500, the plurality of close-up lenses 541 and 542 may be combined to be aligned with the rear camera 510.

Figure 6A:
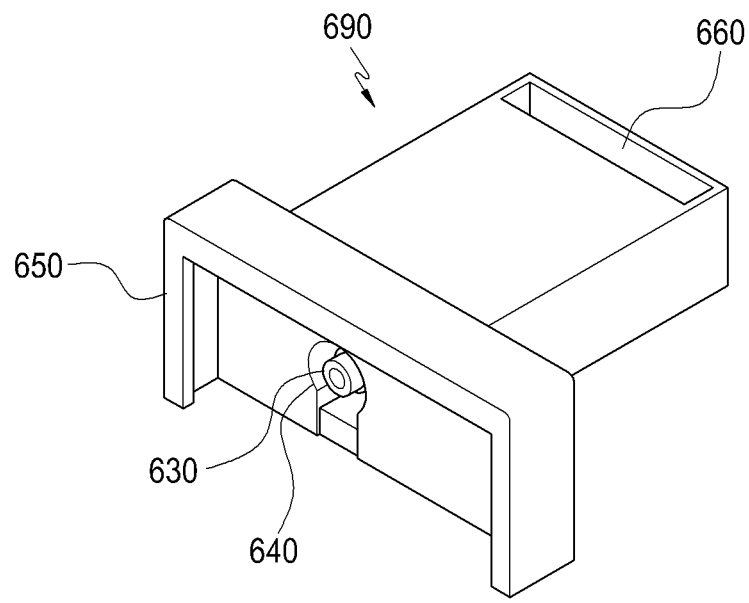
FIGS. 6A and 6B are views illustrating a health information detection device according to various embodiments of the present disclosure.
Figure 6B:
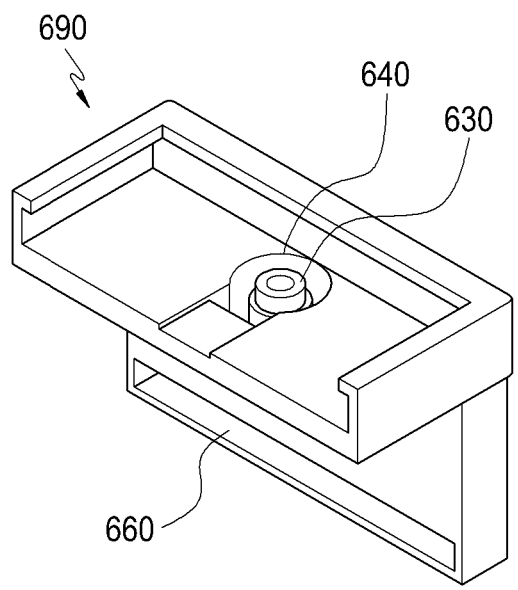

FIGS. 6A and 6B are views illustrating a health information detection device according to various embodiments of the present disclosure.

Referring to FIGS. 6A and 6B, the health information detection device 690 may include a close-up lens 630, a transparent frame 640 formed to surround the close-up lens 630, an electronic device fastening frame 650 configured to fasten an electronic device (e.g., the electronic device 500, shown in FIGS. 5A and 5B), and a strip sensor holder inlet 660 for combining a bio marker obtaining device having a plurality of strip sensors with the health information detection device 690.

According to an embodiment of the present disclosure, referring to FIGS. 6A and 6B, the close-up lens 630 may detect bio marker included in the plurality of strip sensors included in the bio marker obtaining device inserted through the strip sensor holder inlet 660 and may have a higher image uniformity and resolution for bio marker upon detecting bio marker than those of normal lenses.

According to an embodiment of the present disclosure, the transparent frame 640 may be formed to be transparent to maximize the uniformity of light exposure by a flash (e.g., the flash 520, shown in FIGS. 5A and 5B) of the electronic device.

Figure 7:
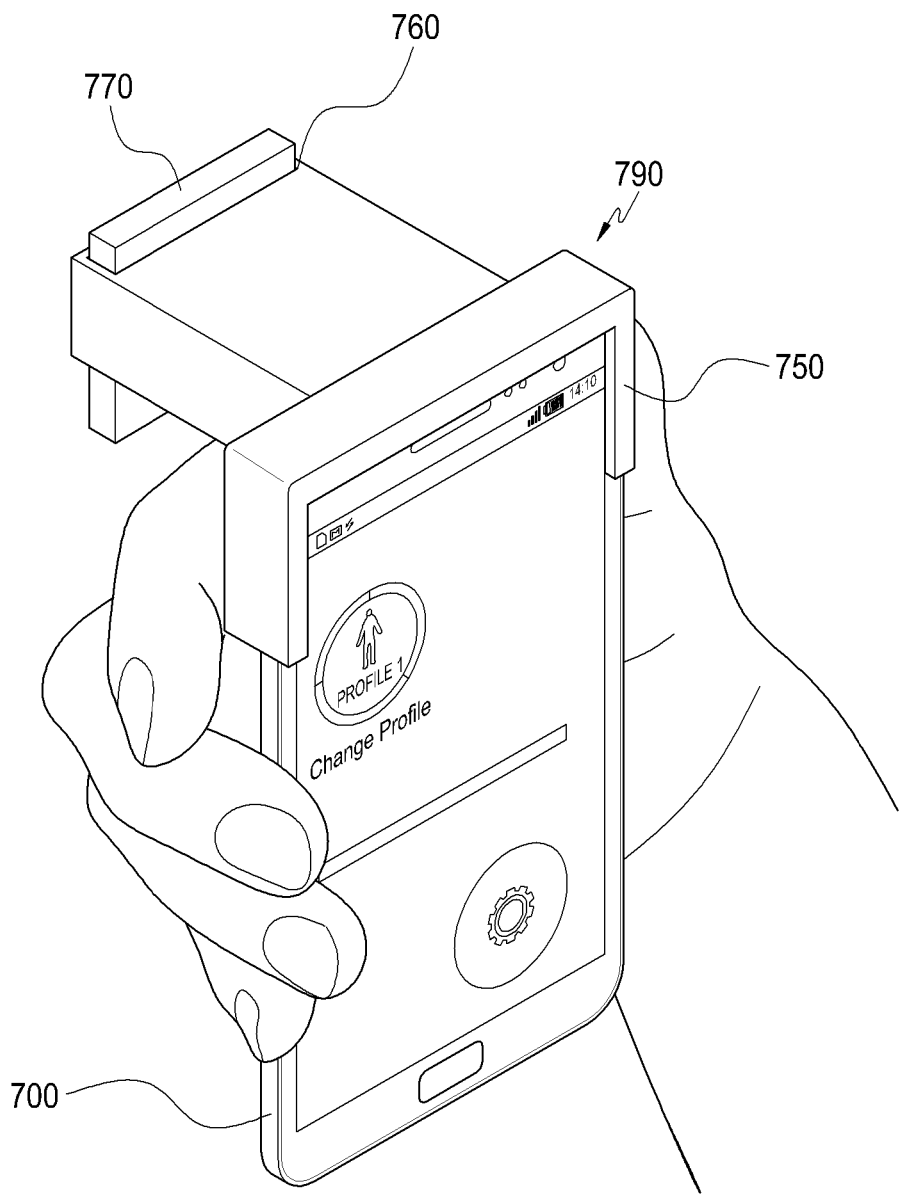
FIG. 7 is a view illustrating an example in which an electronic device, bio marker obtaining device, and health information detection device are combined together according to various embodiments of the present disclosure.

FIG. 7 is a view illustrating an example in which an electronic device, bio marker obtaining device, and health information detection device are combined together according to various embodiments of the present disclosure.

Referring to FIG. 7, according to an embodiment of the present disclosure, the electronic device 700 may be coupled and fastened with a health information detection device 790 through an electronic device fastening frame 750. For example, the electronic device 700 may detect whether to couple with the health information detection device 790 through a sensor module (e.g., the sensor module 240). According to an embodiment of the present disclosure, the bio marker obtaining device 770 may be coupled with the health information detection device 790 through a strip sensor holder inlet 760 of the health information detection device 790.

According to an embodiment of the present disclosure, when the electronic device 700 couples with the health information detection device 790, and the bio marker obtaining device 760 couples with the health information detection device 790, the rear camera (e.g., the rear camera 510, shown in FIGS. 5A and 5B) of the electronic device may be aligned with a close-up lens (e.g., the close-up lens 541 and/or 542, shown in FIGS. 5A and 5B) of the health information detection device. The rear camera 510 may detect bio marker included in a plurality of strip sensors included in the bio marker obtaining device 760 while aligned with the close-up lens 541 and/or 542.

Figure 8:
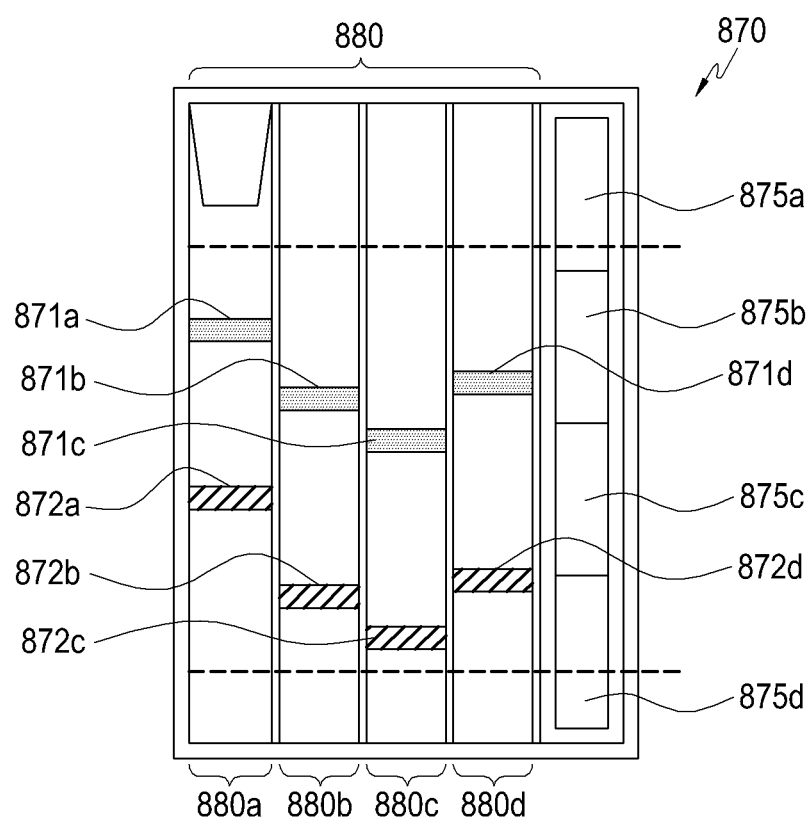
FIG. 8 is a view illustrating a bio marker obtaining device according to various embodiments of the present disclosure.

FIG. 8 is a view illustrating a bio marker obtaining device according to various embodiments of the present disclosure.

Referring to FIG. 8, the bio marker obtaining device 870 may include strip sensors 880 and reference color indicators 875*a*, 875*b*, 875*c*, and 875*d*.

According to an embodiment of the present disclosure, the strip sensors 880 may include a first strip sensor 880*a*, a second strip sensor 880*b*, a third strip sensor 880*c*, and a fourth strip sensor 880*d* configured to obtain their respective pieces of bio marker. According to an embodiment of the present disclosure, the first strip sensor 880*a* may include a first determination section 871*a* for determining the content information on a first bio marker and a first detection section 872*a* for obtaining the bio marker. The same description may also apply to the other strip sensors, i.e., the second strip sensor 880*b*, third strip sensor 880*c*, and fourth strip sensor 880*d*. In particular, the second strip sensor 880*b* may include a first determination section 871*b* for determining the content information on a second bio marker and a first detection section 872*b* for obtaining the bio marker. The third strip sensor 880*c* may include a first determination section 871*c* for determining the content information on a third bio marker and a first detection section 872*c* for obtaining the bio marker. The fourth strip sensor 880*d* may include a first determination section 871*d* for determining the content information on a fourth bio marker and a first detection section 872*d* for obtaining the bio marker.

According to an embodiment of the present disclosure, the reference color indicators may include a reference color indicator 875*a*, a second reference color indicator 875*b*, a third reference color indicator 875*c*, and a fourth reference color indicator 875*d*. The first reference color indicator may display a first reference color for standardizing first bio marker obtained by the first strip sensor 880*a*. The same description may apply to the second, third, and fourth reference color indicators 875*b*, 875*c*, and 875*d* as well.

Figure 9:
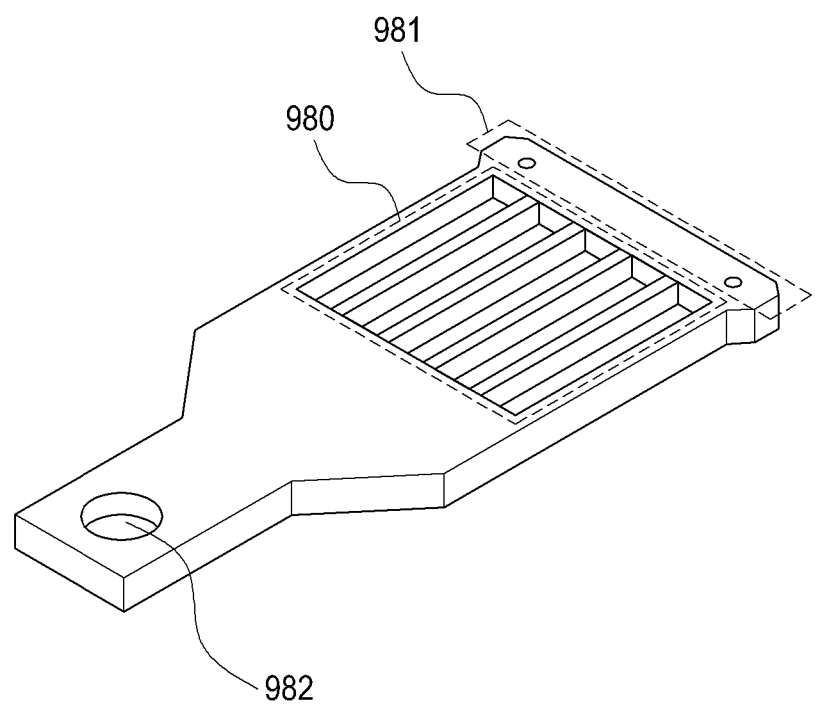
FIGS. 9 and 10 are views illustrating a bio marker obtaining device according to various embodiments of the present disclosure.
Figure 10:
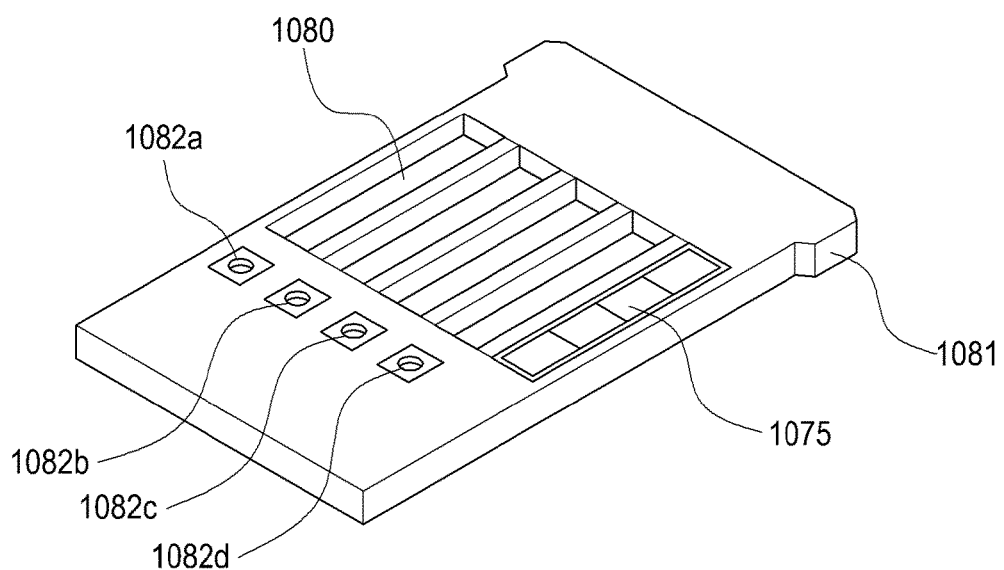

FIGS. 9 and 10 are views illustrating a bio marker obtaining device according to various embodiments of the present disclosure.

Referring to FIG. 9, the bio marker obtaining device (e.g., the bio marker obtaining device 870) may include a plurality of strip sensors 980, a strip sensor holder 981, and a saliva injection hole 982. The bio marker obtaining device may be designed so that when the user's saliva is injected through the saliva injection hole 982, the user's saliva flows through the saliva injection hole 982 to the plurality of strip sensors 980. The strip sensor holder 981 may be formed so that the bio marker obtaining device 870 may be combined with a health information detection device (e.g., the health information detection device 690, shown in FIGS. 6A and 6B).

Referring to FIG. 10, the bio marker obtaining device (e.g., the bio marker obtaining device 870, shown in FIG. 8) may be designed to include a strip sensor holder 1081, a plurality of saliva injection holes 1082*a*, 1082*b*, 1082*c*, and 1082*d* positioned on the strip sensor holder 1081, allowing saliva to be injected to each of the strip sensors 1080.

Figure 11:
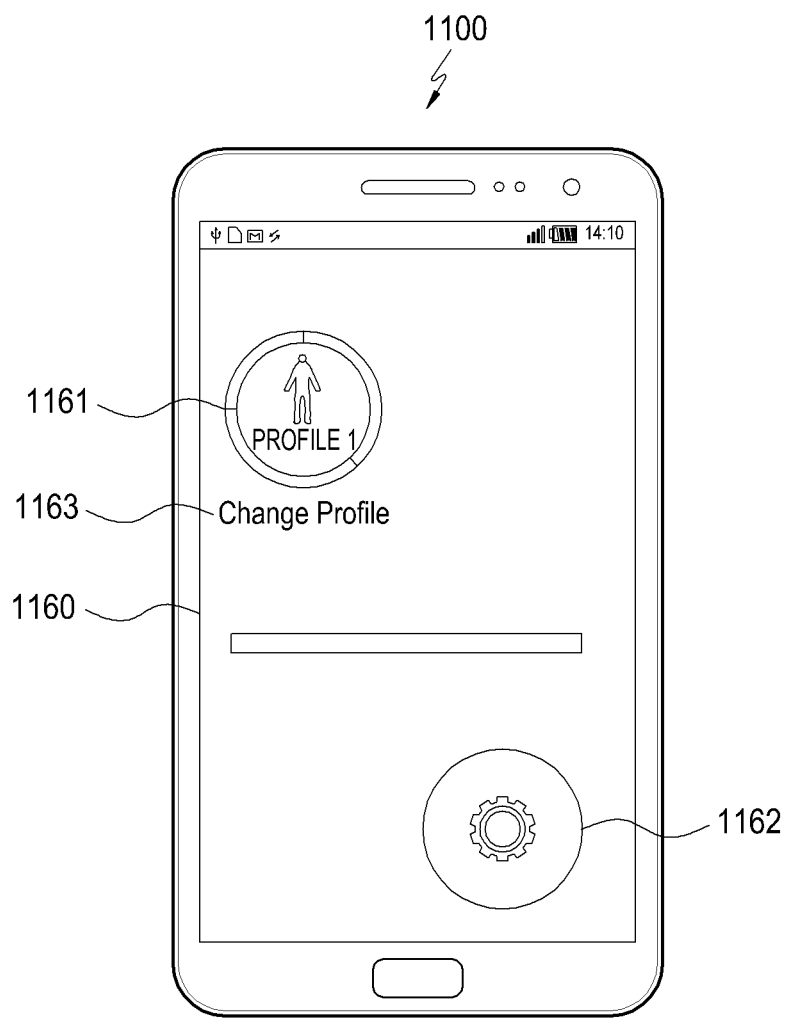
FIG. 11 is a view illustrating an electronic device displaying a health information generation screen according to various embodiments of the present disclosure.

FIG. 11 is a view illustrating an electronic device displaying a health information generation screen according to various embodiments of the present disclosure.

Referring to FIG. 11, the electronic device 1100 may run an application for generating health information (simply, "health information generation app") in response to the user's entry request and may display an execution screen of the running health information generation app through the display 1160. The execution screen of the health information generation app may include user profile information 1161, a change profile tab 1163, and a health information setting tab 1162. The user profile information 1161 may include profile information on the user requesting to generate health information. The change profile tab 1163 may be a tab to receive an input for changing the user profile information. The health information setting tab 1162 may be a tab to select the type of health information.

Figure 12:
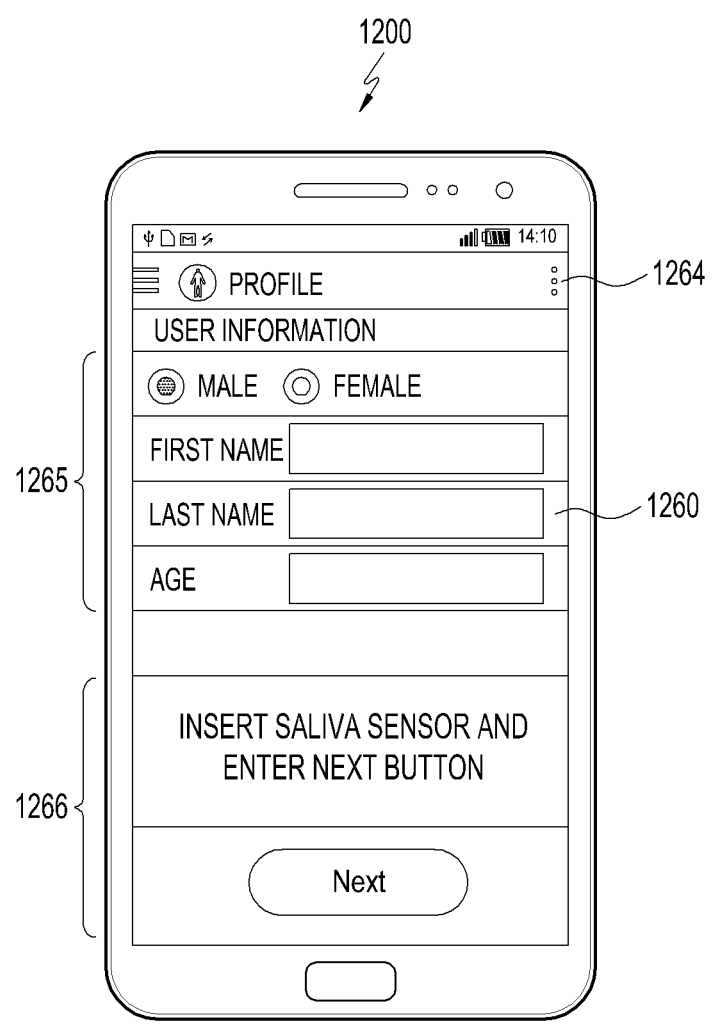
FIG. 12 is a view illustrating an electronic device according to various embodiments of the present disclosure.

FIG. 12 is a view illustrating an electronic device according to various embodiments of the present disclosure.

Referring to FIG. 12, the display 1260 of the electronic device 1200 may display an example screen of a health information generation app. Upon receiving an input through the change profile tab 1163 of FIG. 11, the electronic device 1200 may display a change user profile screen as an example of the health information generation app screen through the display 1260.

According to an embodiment of the present disclosure, the change profile screen may include a profile title tab 1264 indicating that the screen is a screen for changing profiles, a user information menu including information on the user's gender, first or last name, or age, and a saliva sensor insertion tab 1266. The electronic device 1200 may change the information on the user's gender, first or last name, or age or display the changed user information based on an input (e.g., a touch input) to the user information menu 1265 in the change profile screen.

Figure 13:
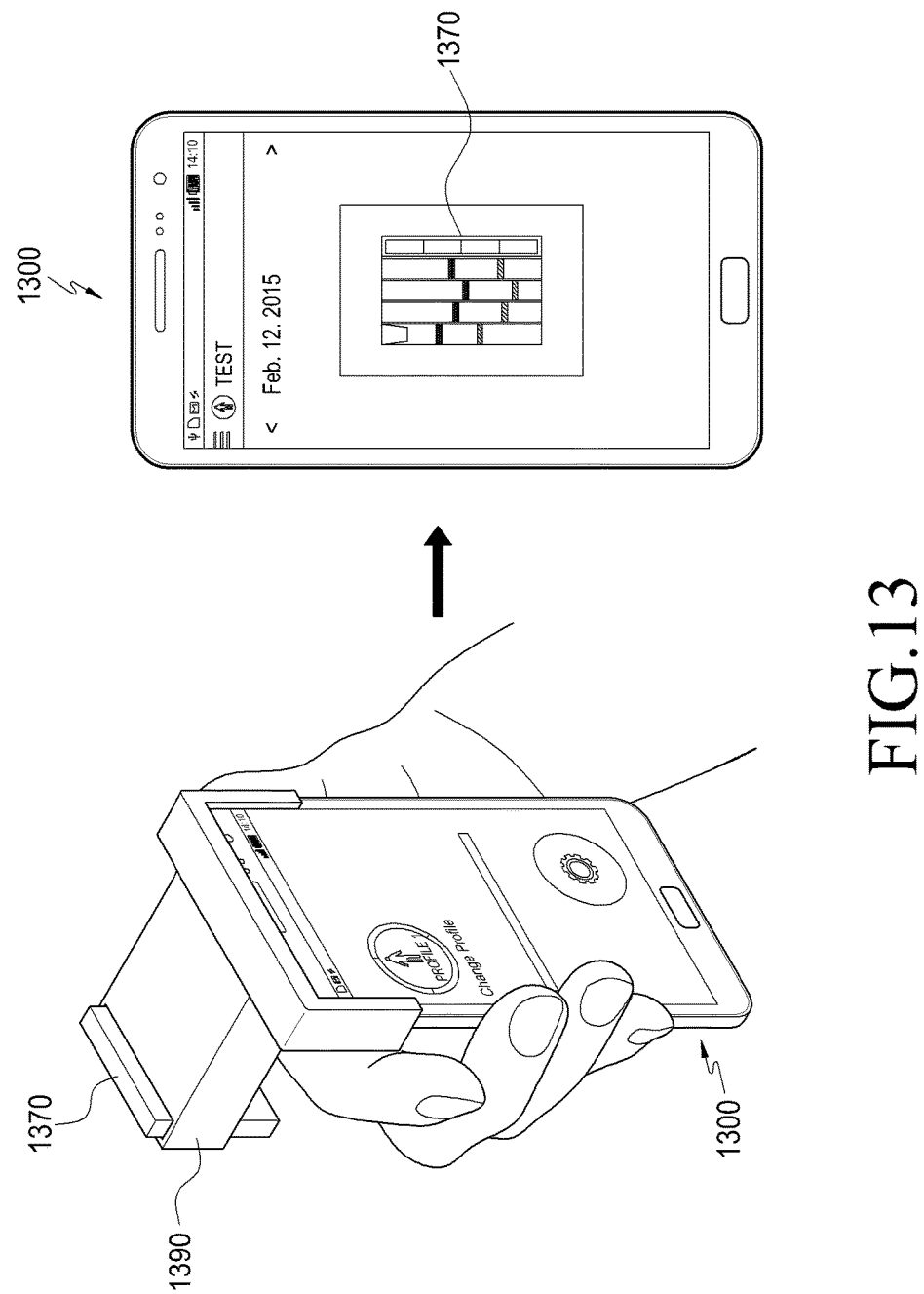
FIG. 13 is a view illustrating a method for detecting a bio marker according to various embodiments of the present disclosure.

FIG. 13 is a view illustrating a method for detecting a bio marker according to various embodiments of the present disclosure.

Referring to FIG. 13, the electronic device 1300 may detect whether the health information detection device 1390 is coupled with the electronic device 1300 and whether the bio marker obtaining device 1370 is coupled with the health information detection device 1390 through a sensor module (e.g., the sensor module 240).

For example, when the health information detection device 1390 couples with the electronic device 1300, the electronic device 1300 may display an execution screen of a health information generation app. When the health information detection device 1390 couples with the electronic device 1300, and the bio marker obtaining device 1370 couples with the health information detection device 1390 while the execution screen of the health information generation app is being displayed, the electronic device 1300 may display a screen for detecting bio markers. The screen for detecting bio markers may include images for a plurality of strip sensors in the bio marker obtaining device 1370 detected through the close-up lens (e.g., the close-up lens 440) of the health information detection device 1390 and the rear camera (e.g., the rear camera 410) of the electronic device 1300.

Figure 14:
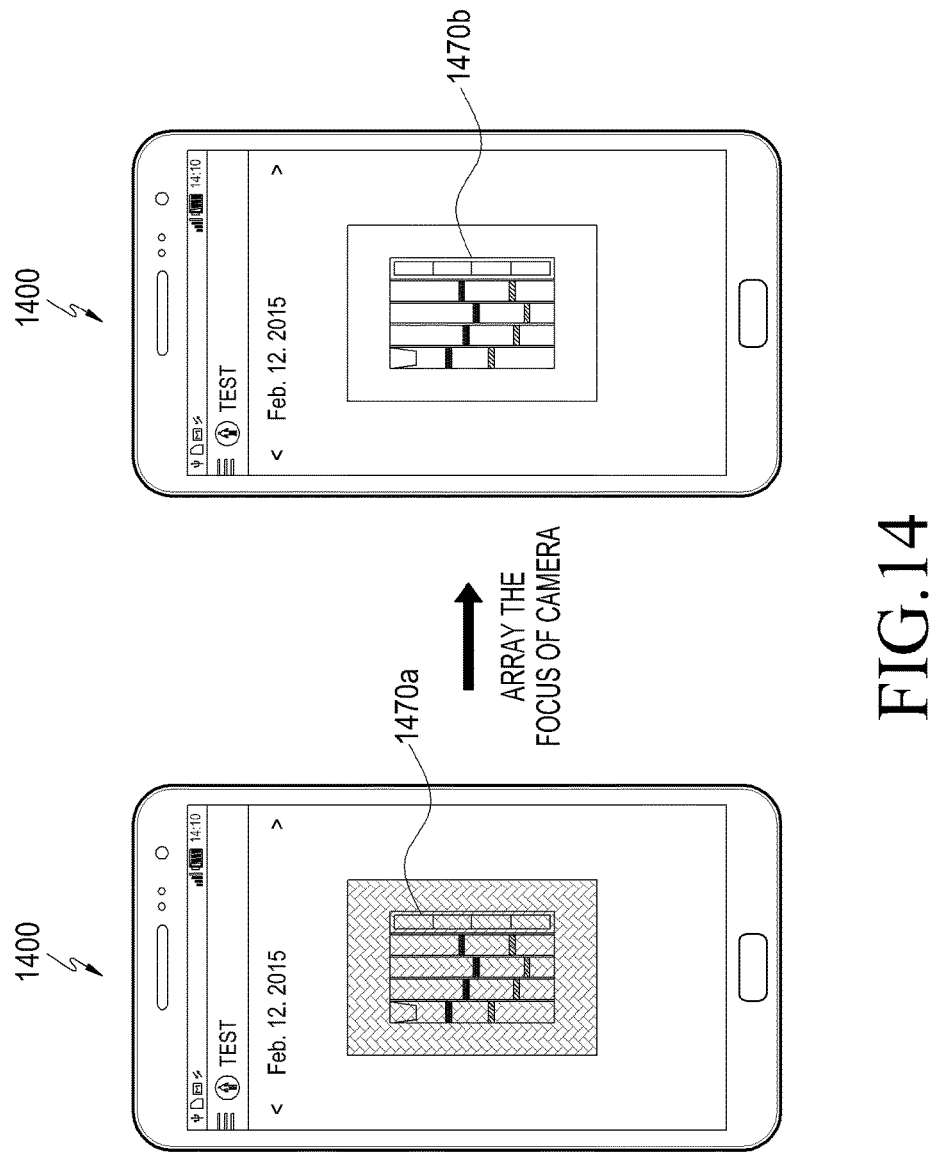
FIG. 14 is a view illustrating a method for focusing strip sensors according to various embodiments of the present disclosure.

FIG. 14 is a view illustrating a method for arraying the focus of the camera to the strip sensors according to various embodiments of the present disclosure.

Referring to FIG. 14, the electronic device 1400 may display a screen for detecting bio markers and recognize a plurality of strip sensors to display a first image 1470*a* for the plurality of strip sensors. According to an embodiment of the present disclosure, the electronic device 1400 may array the focus the first image for the plurality of strip sensors while the first image 1470*a* for the plurality of strip sensors is being displayed and display a second image 1470*b* for the plurality of strip sensors.

Figure 15:
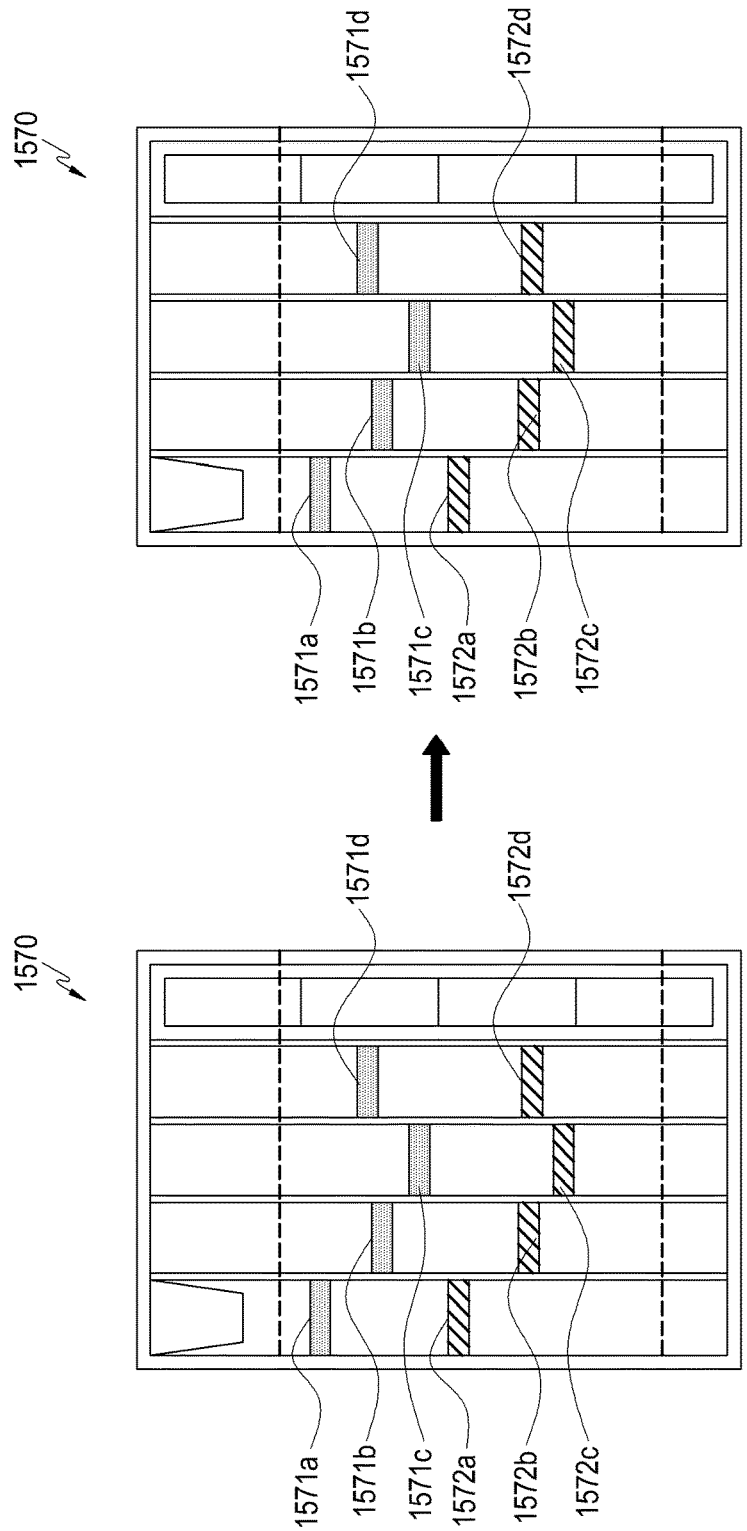
FIG. 15 is a view illustrating a method for identifying a determination section according to various embodiments of the present disclosure.

FIG. 15 is a view illustrating a method for identifying a determination section according to various embodiments of the present disclosure.

Referring to FIG. 15, the electronic device (e.g., the electronic device 1500) may display an image (e.g., the second image 1470b, shown in FIG. 14) for the bio marker obtaining device 1570 and may detect the respective measurement values (e.g., brightness values, gray scale values, red values, green values, and blue values) of the strip sensors (e.g., the first strip sensor, second strip sensor, third strip sensor, and fourth strip sensor) included in the second image 1470b. For example, the electronic device 1500 may detect a measurement value for the first strip sensor, detect a plurality of particular sections 1571a and 1572a where the measurement value is not more than a preset first measurement value. The same operation may apply to the other strip sensors, i.e., the second, third, and fourth strip sensors. For example, the electronic device 1500 may identify a section 1571a having a larger measurement value among the plurality of particular sections detected as a first determination section. For example, the electronic device 1500 may identify the sections 1571b, 1571c, and 1571d having larger measurement values among the plurality of particular sections where the measurement values respectively detected from the second, third, and fourth strip sensors are not less than the preset first measurement value as the second determination section, third determination section, and fourth determination section, respectively.

Figure 16:
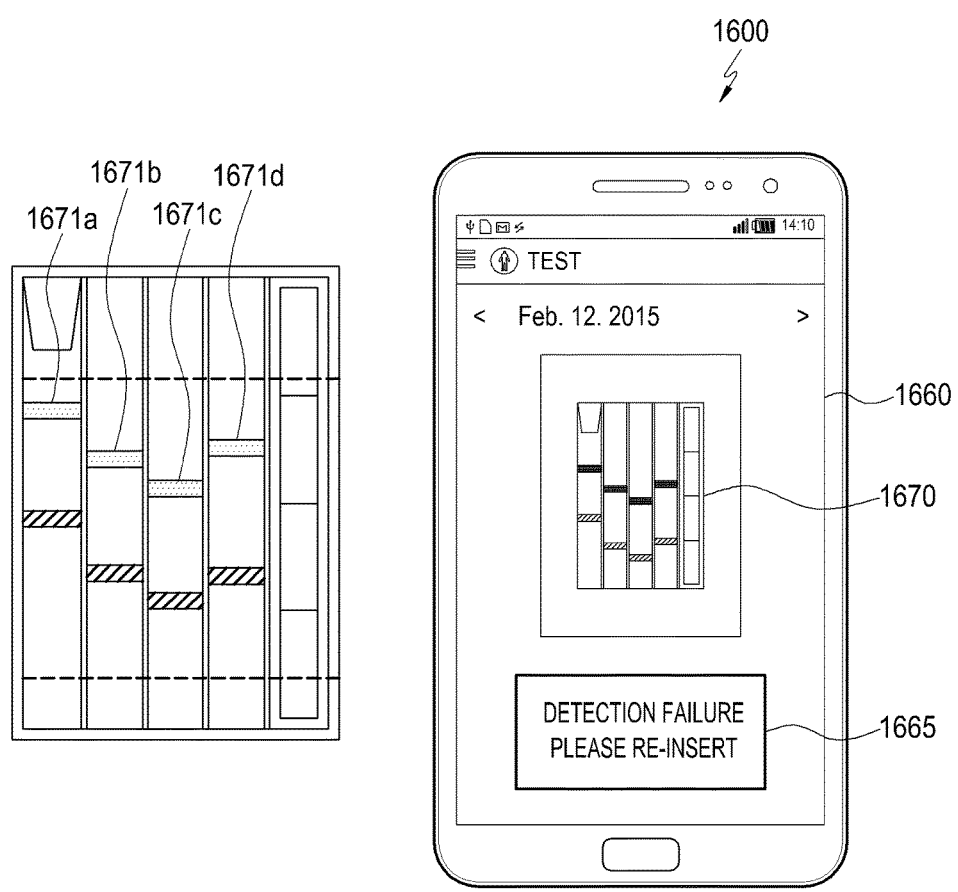
FIG. 16 is a view illustrating a method for determining whether to obtain a bio marker according to various embodiments of the present disclosure.

FIG. 16 is a view illustrating a method for determining whether to obtain a bio marker according to various embodiments of the present disclosure.

Referring to FIG. 16, the electronic device (e.g., the electronic device 1600) may detect the representative value (e.g., mean, median, or mode value) of the measurement values in each of the plurality of identified first determination section 1671a, second determination section 1671b, third determination section 1671c, and fourth determination section 1671d. According to an embodiment of the present disclosure, the electronic device 1600 may determine whether the representative value of the measurement values in each of the plurality of first determination section 1671a, second determination section 1671b, third determination section 1671c, and fourth determination section 1671d is not less than a preset second measurement value.

According to an embodiment of the present disclosure, when the representative value of the measurement values in any one or more of the first determination section 1671a, second determination section 1671b, third determination section 1671c, and fourth determination section 1671d is not less than the preset second measurement value, the electronic device 1600 may determine that the recognition for the plurality of strip sensors 1670 fails and display detection failure information 1665 stating "Detection fails. Please insert again" through the display 1660.

According to an embodiment of the present disclosure, with reference to FIG. 16, as an example, when the representative value of the measurement values in all of the first determination section 1671a, second determination section 1671b, third determination section 1671c, and fourth determination section 1671d is not more than the preset second measurement value, the electronic device 1600 may determine that the recognition for the plurality of strip sensors 1670 succeeds and identify a first detection section, second detection section, third detection section, and fourth detection section based on a plurality of particular sections having smaller measurement values than the determination sections (e.g., the first determination section 1671a, second determination section 1671b, third determination section 1671c, and fourth determination section 1671d) among a plurality of particular sections detected.

FIGS. 17 and 18 are views illustrating a method for identifying a detection section according to various embodiments of the present disclosure.

According to an embodiment of the present disclosure, the electronic device (e.g., the electronic device 1600, shown in FIG. 16) may detect the distance between pre-identified first determination sections 1771a and 1871a and particular sections 1772a and 1872a having smaller measurement values than those of the pre-identified first determination sections. According to an embodiment of the present disclosure, the electronic device 1600 may determine whether the distance between pre-identified first determination sections 1771a and 1871a detected and the particular sections 1772a and 1872a having smaller measurement values than those of the pre-identified first determination sections is not less than predetermined distances 1771e and 1871e.

Referring to FIG. 17, according to an embodiment of the present disclosure, when the distance between the first determination section 1771a and the particular section 1772a having a smaller measurement value than that of the first determination section is not more than a predetermined distance 1771e, the electronic device 1600 (shown in FIG. 16) may identify the particular section 1772a having a smaller measurement value than the first determination section as the first detection section 1772a of the first strip sensor.

Referring to FIG. 18, according to an embodiment of the present disclosure, when the distance between the first determination section 1871a and the particular section 1872a having a smaller measurement value than that of the first determination section is not less than a predetermined distance 1871e, the electronic device 1600 (shown in FIG. 16) may identify a section spaced apart from the first determination section 1871a at a predetermined interval as the first determination section 1873a. According to an embodiment of the present disclosure, the method for identifying the first detection section may apply likewise to identification of the second, third, and fourth detection section.

Figure 19:
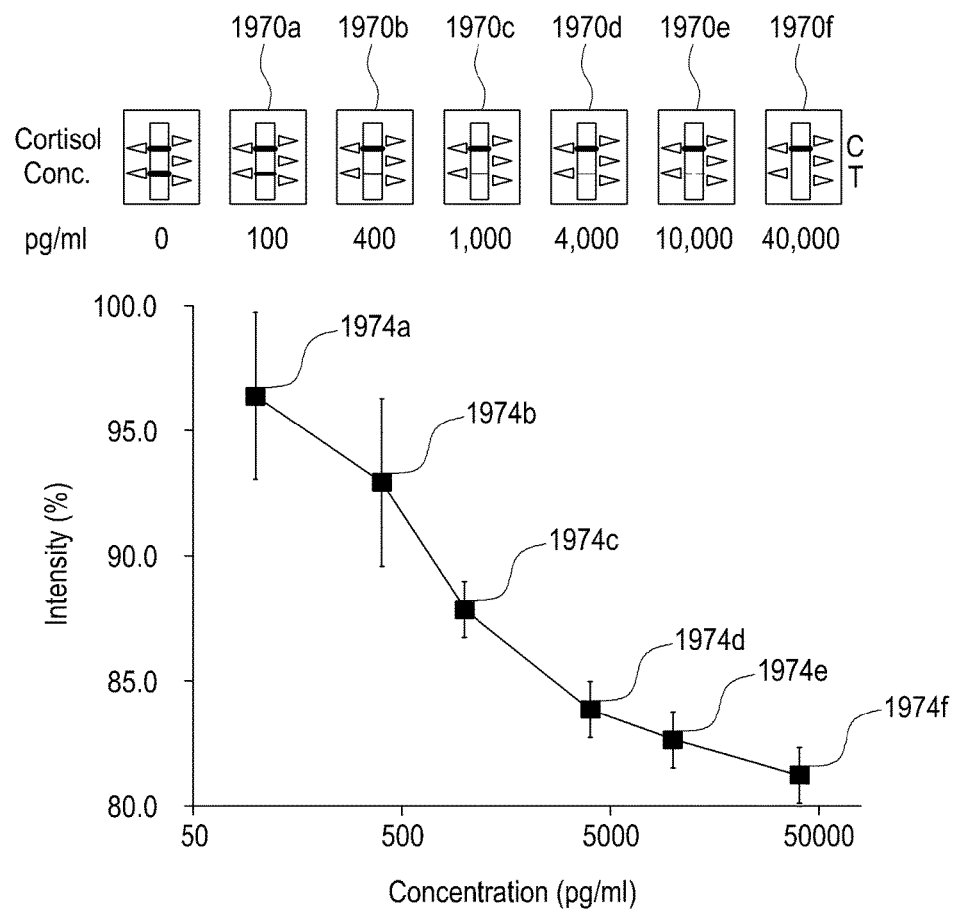
FIG. 19 is a graph illustrating an example of a bio marker according to various embodiments of the present disclosure.

FIG. 19 is a graph illustrating an example of a bio marker according to various embodiments of the present disclosure.

Referring to FIG. 19, the bio marker may include cortisol. The concentration of cortisol may be represented in pg/ml, and examples of the content of cortisol may include 0 pg/ml, 100 pg/ml, 400 pg/ml, 1000 pg/ml, 10000 pg/ml, or 40000 pg/ml. Strip sensor 1970a, 1970b, 1970c, 1970d, 1970e, or 1970f may indicate concentration information on the cortisol (an example of the bio marker) included in each strip sensor.

According to an embodiment of the present disclosure, the electronic device (e.g., the electronic device 1600, shown in FIG. 16) may compute the representative value of the measurement values in the pre-identified detection section. For example, when the representative value of the measurement values in the first detection section in the first strip sensor is computed, the electronic device 1600 may standardize the computed representative value of the measurement values in the first detection section based on the first reference color corresponding to the first bio marker among reference colors displayed on the reference color indicators (e.g., the reference color indicator 1075, shown in FIG. 10). When the representative value of the measurement values in the first detection section is standardized as a standardized measurement value based on the first reference color, the electronic device 1600 may convert a representative value of the standardized measurement value into the concentration of the first bio marker.

For example, when one strip sensor contains 400 pg/ml of cortisol (an example of the first bio marker), the first strip sensor obtaining the cortisol may be in the form of the first strip sensor 1970*b*, and the representative value of the measurement values shown in the first detection section of the first strip sensor may indicate the first measurement value 1974*b*. For example, when the representative value of the first measurement value in the first detection section included in the first strip sensor 1970*b* computed by the electronic device 1600 is 93%, the electronic device 1600 may standardize the representative value (93%) of the first measurement value based on a cortisol reference color corresponding to the cortisol and convert the standardized representative value of measurement value into the concentration (400 pg/ml) of the cortisol. Other strip sensors 1974*a*, 1974*c*, 1974*e* and 1974*f* have corresponding measurement values, as detailed in the graph shown in FIG. 19.

FIGS. 20A, 20B, 20C, 21A, 21B, and 21C are views illustrating a method for generating health information according to various embodiments of the present disclosure.

Referring to FIG. 20A, the electronic device 2000 may display a pre-recognized image for a plurality of strip sensors 2070 included in the bio marker obtaining device through the display 2060 and may obtain the concentration of the plurality of bio markers included in the plurality of strip sensors 2070 based on the recognized image of the plurality of strip sensors 2070 by the method described above in connection with FIG. 19.

Referring to FIG. 20B, according to an embodiment of the present disclosure, the electronic device 2000 may display the concentration information 2068 on the plurality of obtained bio markers through the display 2060.

Referring to FIG. 20C, the electronic device 2000 may generate user health information 2068 indicating that the user is in a normal health condition based on the concentration information 2068 on the plurality of obtained bio markers and display the generated user health information 2069 through the display 2060.

Figure 21C:
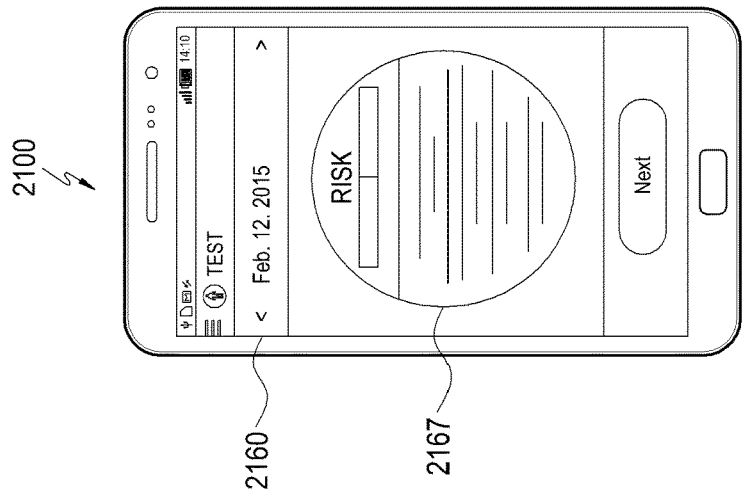
Figure 21B:
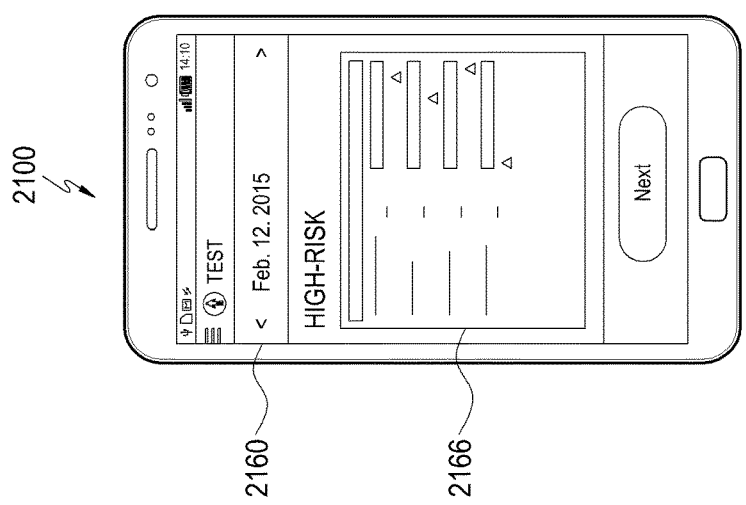
Figure 21A:
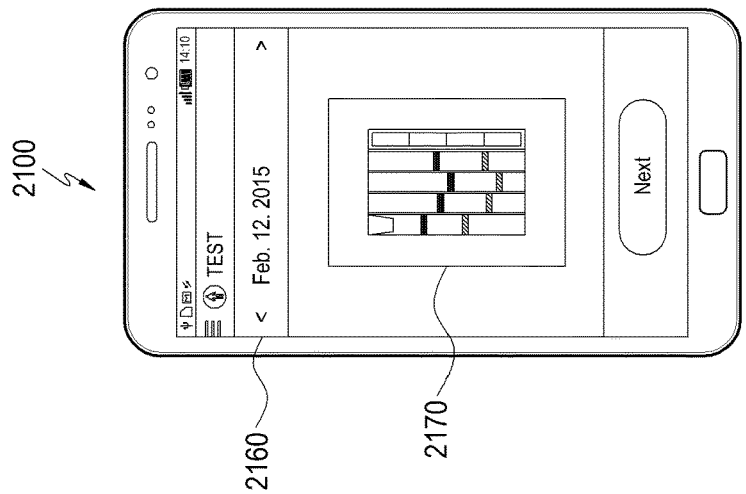

Referring to FIG. 21A, the electronic device 2100 may display a pre-recognized image for a plurality of strip sensors 2170 included in the bio marker obtaining device through the display 2160 and may obtain the concentration of the plurality of bio markers included in the plurality of strip sensors 2170 based on the recognized image of the plurality of strip sensors 2170 by the method described above in connection with FIG. 19.

Referring to FIG. 21B, the electronic device 2100 may display the concentration information 2166 on the plurality of previously obtained bio markers through the display 2160.

Referring to FIG. 21C, the electronic device 2100 may generate user health information 2167 indicating that the user is in a risky health condition based on the concentration information 2067 on the plurality of obtained bio markers and display the generated user health information 2067 through the display 2160.

Figure 22A:
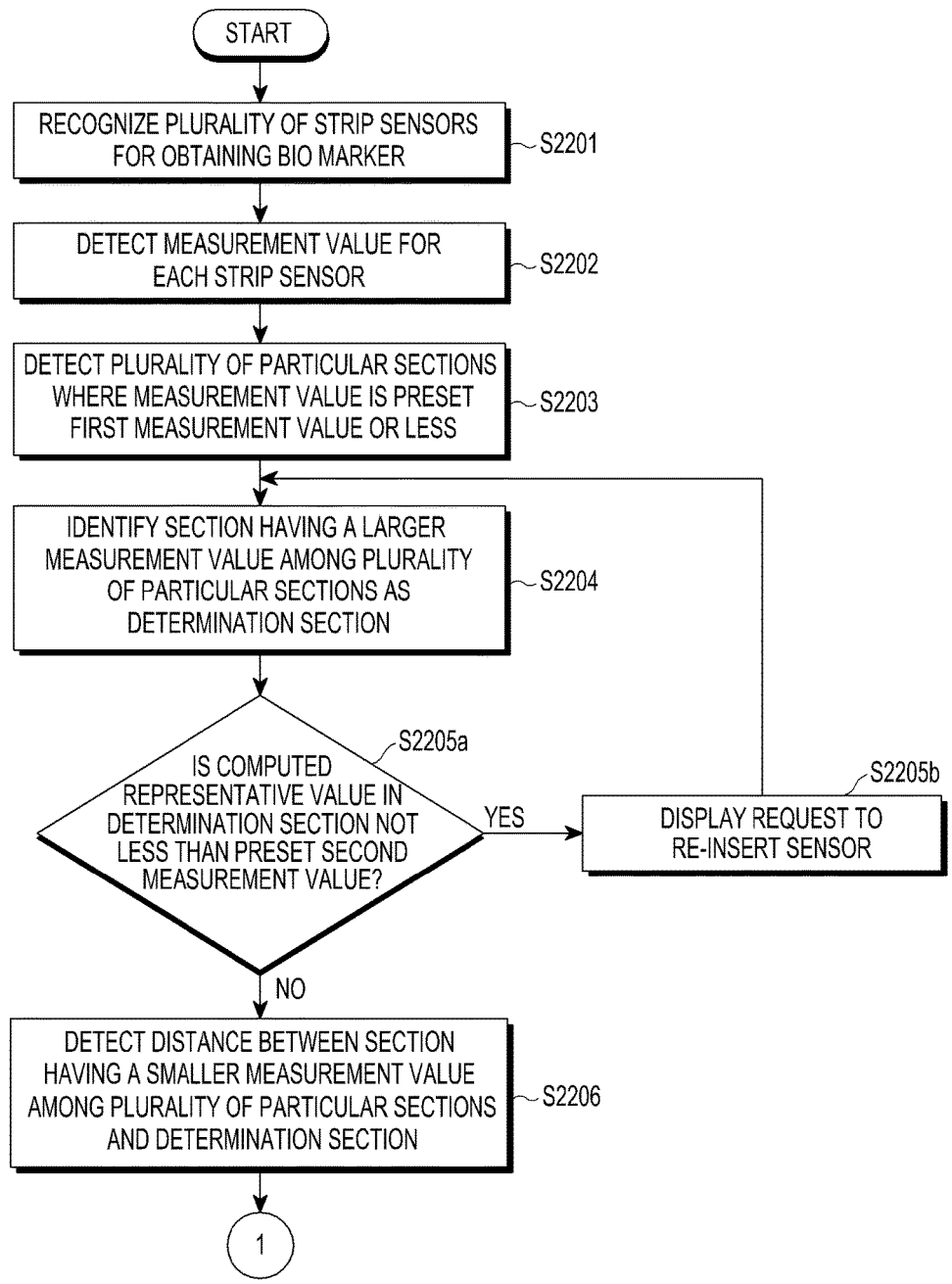
FIGS. 22A and 22B are views illustrating a method for generating bio marker according to various embodiments of the present disclosure.
Figure 22B:
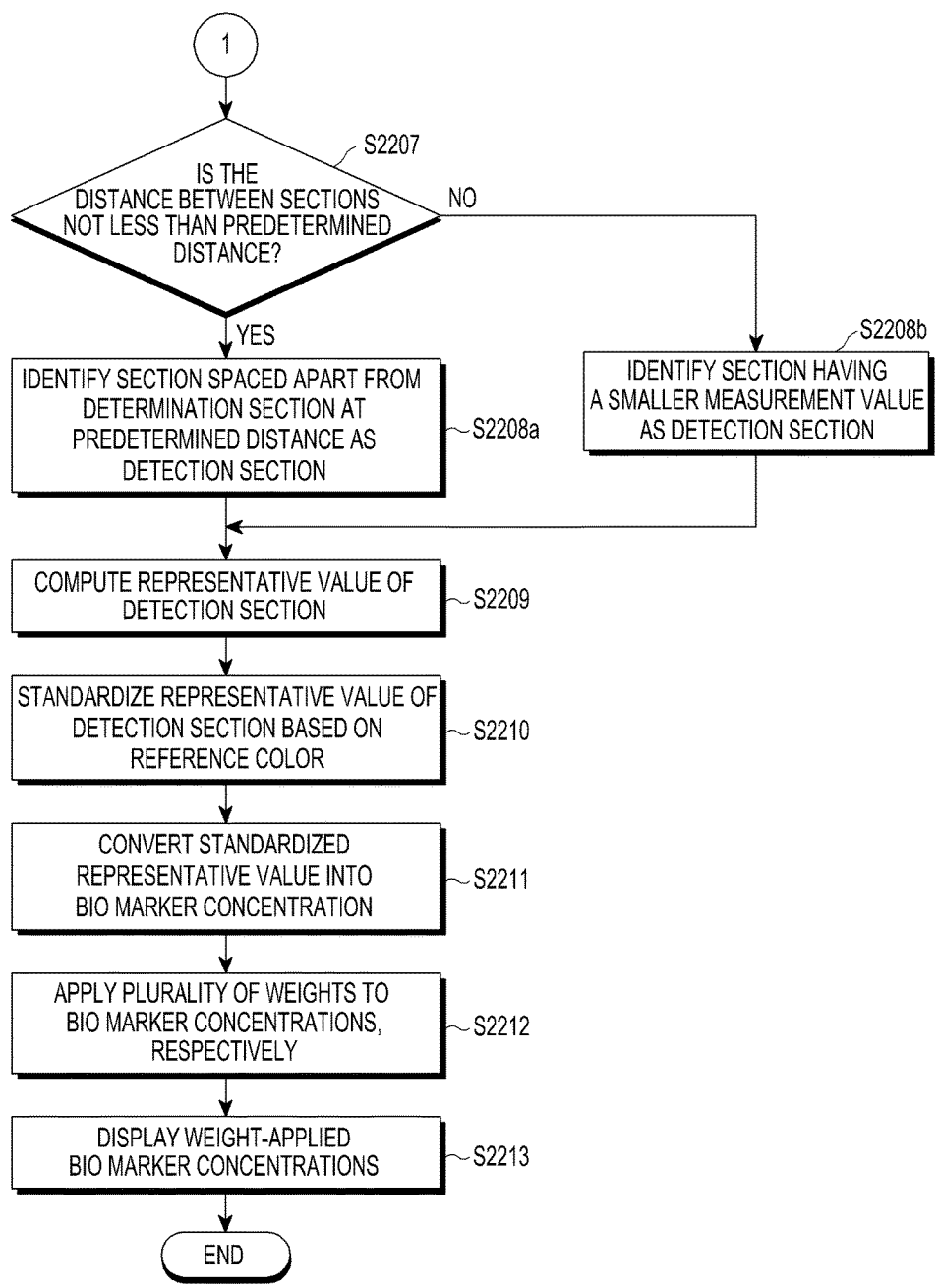

FIGS. 22A and 22B are views illustrating a method for generating bio marker according to various embodiments of the present disclosure.

Referring to FIGS. 22A and 22B, in operation S2201, shown in FIG. 22A, the electronic device (e.g., the electronic device 101) may recognize a plurality of strip sensors to obtain bio markers.

In operation S2202, referring to FIG. 22A, the electronic device may detect measurement values for the recognized strip sensors, respectively.

In operation S2203, the electronic device may detect a plurality of particular sections where the detected measurement values are not more than a preset first measurement value.

In operation S2204, the electronic device may identify a section having larger measurement values among the plurality of particular sections as a determination section.

In operation S2205*a*, the electronic device may compute a representative value of the measurement values in the determination section and determine whether the computed representative value is not less than the preset second measurement value.

In operation S2205*b*, when the representative value of the measurement values in the determination section is not less than the second measurement value, the electronic device may determine that the recognition is failed and may display request information for requesting to re-insert the sensors.

In operation S2206, referring to FIG. 22A, when the representative value of the measurement values in the determination section is not more than the second measurement value, the electronic device may determine that the recognition succeeds and detect the distance between a pre-identified determination section among the plurality of particular sections and another one of the remaining sections having smaller measurement values than that of the determination section.

With reference to FIG. 22B, in operation S2207, the electronic device may determine whether the distance between the pre-identified determination section and the other section having a smaller measurement value than that of the determination section is not less than a predetermined distance.

In operation S2208*b*, referring to FIG. 22B, when the distance between the pre-identified determination section and the other section having a smaller measurement value than that of the determination section is not more than the predetermined distance, the electronic device may identify the other section having the smaller measurement value as a detection section.

In operation S2208*a*, when the distance between the pre-identified determination section and the other section having a smaller measurement value than that of the determination section is not less than the predetermined distance, the electronic device may identify a section spaced apart from the determination section at a predetermined interval as a detection section.

In operation S2209, the electronic device may compute the representative value of measurement values in the identified detection section.

In operation S2210, the electronic device may standardize the computed representative value of the measurement values in the detection section based on a reference color.

In operation S2211, referring to FIG. 22B, the electronic device may convert the standardized representative value of measurement values into the concentration of the bio marker.

In operation S2212, the electronic device may apply each of the plurality of weights to the each of the plurality of concentrations, respectively, obtained for the plurality of bio markers in operation S2211 and its precedent operations.

In operation S2213, the electronic device may display the plurality of weight-applied bio marker concentrations.

According to various embodiments of the present disclosure, a bio marker detection device for detecting a bio marker from a plurality of strip sensors may comprise a close-up lens for detecting an image for the plurality of strip sensors, a transparent frame surrounding the close-up lens to evenly pass light from an external source or an outside to the plurality of strip sensors, and a strip sensor holder inlet formed to combine the plurality of strip sensors with the bio marker detection device.

According to various embodiments of the present disclosure, the bio marker detection device may further comprise a fastening frame formed to combine an electronic device including a camera configured to obtain an image for the bio marker.

According to various embodiments of the present disclosure, a method for generating health information from a plurality of strip sensors may comprise detecting information on a plurality of bio markers from a plurality of sensors, generating user health information based on the detected information on the plurality of detected bio markers, and displaying the generated user health information.

According to various embodiments of the present disclosure, detecting the information on the plurality of bio markers from the plurality of sensors may include recognizing the plurality of strip sensors for obtaining the plurality of bio markers, identifying a plurality of detection sections in each of the plurality of recognized strip sensors, and detecting the information on the plurality of bio markers from each of the plurality of detection sections.

According to various embodiments of the present disclosure, recognizing the plurality of strip sensors for obtaining the plurality of bio markers may include determining whether the plurality of strip sensors is detected by a camera, and when the plurality of strip sensors is detected, focusing the camera for the plurality of strip sensors.

According to various embodiments of the present disclosure, identifying the plurality of detection sections in each of the plurality of recognized strip sensors may include identifying a determination section in each of the plurality of strip sensors, computing a representative value of a measurement value in the identified determination section, and when the computed representative value of the measurement value in the determination section is not less than a preset first measurement value, displaying a request for re-inserting the strip sensor.

According to various embodiments of the present disclosure, identifying the determination section in each of the plurality of strip sensors may include identifying a plurality of particular sections where the measurement value in each strip sensor is not more than a preset second measurement value and identifying a particular section having a larger measurement value among the plurality of identified particular sections as the determination section.

According to various embodiments of the present disclosure, identifying the plurality of detection sections in each of the plurality of recognized strip sensors may include detecting a measurement value for each of the plurality of strip sensor, identifying a plurality of particular sections where the measurement value in each strip sensor is not more than a preset second measurement value, and identifying a detection section among the plurality of identified particular sections according to a predetermined condition.

According to various embodiments of the present disclosure, identifying the detection section among the plurality of identified particular sections according to the predetermined condition may include identifying a particular section having a larger measurement value among the identified particular sections as the determination section, when a distance between a particular section having a smaller measurement value among the identified particular sections and the identified determination section is not less than a predetermined distance, identifying a particular section spaced apart from the determination section at the predetermined distance as the detection section, and when the distance between the particular section having the smaller measurement value among the identified particular sections and the identified determination section is not more than the predetermined distance, identifying the particular section having the smaller measurement value as the detection section.

According to various embodiments of the present disclosure, detecting the information on the plurality of bio markers from each of the plurality of detection sections may include computing a representative value of a measurement value in the detection section, standardizing the computed representative value of the measurement value in the detection section based on a reference color set for each of the plurality of bio markers, converting the standardized representative value of the measurement value into a concentration of the bio marker, applying each of the plurality of preset weights to each of the plurality of converted bio marker concentrations, respectively, and displaying the weight-applied bio marker concentrations.

According to various embodiments of the present disclosure, an electronic device generating health information from a plurality of strip sensors may comprise a camera sensor detecting information on a plurality of bio markers from a plurality of sensors, a processor generating user health information based on the detected information on the plurality of detected bio markers, and a display displaying the generated user health information.

According to various embodiments of the present disclosure, the camera sensor may recognize the plurality of strip sensors for obtaining the plurality of bio markers, identify a plurality of detection sections in each of the plurality of recognized strip sensors, and detect the information on the plurality of bio markers from each of the plurality of detection sections.

According to various embodiments of the present disclosure, the process may identify a determination section in each of the plurality of strip sensors and compute a representative value of a measurement value in the identified determination section, and the display, when the computed representative value of the measurement value in the determination section is not less than a preset first measurement value, may display a request for re-inserting the strip sensor.

According to various embodiments of the present disclosure, the processor may identify a plurality of particular sections where the measurement value in each strip sensor is not more than a preset second measurement value and identify a particular section having a larger measurement value among the plurality of identified particular sections as the determination section.

According to various embodiments of the present disclosure, the processor may detect a measurement value for each of the plurality of strip sensor, identify a plurality of particular sections where the measurement value in each strip sensor is not more than a preset second measurement value, and identify a detection section among the plurality of identified particular sections according to a predetermined condition.

According to various embodiments of the present disclosure, the processor may identify a particular section having a larger measurement value among the identified particular sections as the determination section, when a distance between a particular section having a smaller measurement value among the identified particular sections and the identified determination section is not less than a predetermined distance, identify a particular section spaced apart from the determination section at the predetermined distance as the detection section, and when the distance between the particular section having the smaller measurement value among the identified particular sections and the identified determination section is not more than the predetermined distance, identify the particular section having the smaller measurement value as the detection section.

According to various embodiments of the present disclosure, the processor may compute a representative value of a measurement value in the detection section, standardize the computed representative value of the measurement value in the detection section based on a reference color set for each of the plurality of bio markers, convert the standardized representative value of the measurement value into a concentration of the bio marker, apply each of the plurality of preset weights to each of the plurality of converted bio marker concentrations, respectively, and display the weight-applied bio marker concentrations. Each of the aforementioned components of the electronic device may include one or more parts, and a name of the part may vary with a type of the electronic device.

The electronic device in accordance with various embodiments of the present disclosure may include at least one of the aforementioned components, omit some of them, or include other additional component(s). Some of the components may be combined into an entity, but the entity may perform the same functions as the components may do.

The term 'module' may refer to a unit including one of hardware, software, and firmware, or a combination thereof. The term 'module' may be interchangeably used with a unit, logic, logical block, component, or circuit. The module may be a minimum unit or part of an integrated component. The module may be a minimum unit or part of performing one or more functions. The module may be implemented mechanically or electronically. For example, the module may include at least one of Application Specific Integrated Circuit (ASIC) chips, Field Programmable Gate Arrays (FPGAs), or Programmable Logic Arrays (PLAs) that perform some operations, which have already been known or will be developed in the future.

According to various embodiments of the present disclosure, at least a part of the device (e.g., modules or their functions) or method (e.g., operations) may be implemented as instructions stored in a computer-readable storage medium e.g., in the form of a program module. The instructions, when executed by a processor (e.g., the processor 120), may enable the processor to carry out a corresponding function. The computer-readable storage medium may be e.g., the memory 130.

The computer-readable storage medium may include a hardware device, such as hard discs, floppy discs, and magnetic tapes (e.g., a magnetic tape), optical media such as compact disc read only memories (ROMs), CD-ROMs and digital versatile discs (DVDs), magneto-optical media such as floptical disks, ROMs, random access memories (RAMs), flash memories, and/or the like. Examples of the program instructions may include not only machine language codes but also high-level language codes which are executable by various computing means using an interpreter. The aforementioned hardware devices may be configured to operate as one or more software modules to carry out various embodiments of the present disclosure, and vice versa.

Modules or programming modules in accordance with various embodiments of the present disclosure may include at least one or more of the aforementioned components, omit some of them, or further include other additional components. Operations performed by modules, programming modules or other components in accordance with various embodiments of the present disclosure may be carried out sequentially, simultaneously, repeatedly, or heuristically. Furthermore, some of the operations may be performed in a different order, or omitted, or include other additional operation(s).

According to various embodiments of the present disclosure, there is provided a storage medium or memory storing instructions configured to be executed by at least one processor to enable the processor to perform at least one operation that may include recognizing the plurality of strip sensors for obtaining the plurality of bio markers, identifying a plurality of detection sections in each of the plurality of recognized strip sensors, and detecting the information on the plurality of bio markers from each of the plurality of detection sections.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A method for generating health information from a plurality of strip sensors, the method comprising:
 detecting a plurality of bio markers from the plurality of strip sensors, wherein the detecting of the plurality of bio markers includes recognizing the plurality of strip sensors and identifying a plurality of detection sections in each of the plurality of strip sensors;
 generating user health information based on the detected plurality of detected bio markers; and
 displaying the generated user health information,
 wherein the identifying of the plurality of detection sections in each of the plurality of strip sensors comprises:
  identifying a determination section in each of the plurality of strip sensors,
  computing a representative value of a first measurement value in the identified determination section, and
  displaying, based on the computed representative value, a request for re-inserting at least one of the plurality of strip sensors.

2. The method of claim 1, wherein the detecting of the plurality of bio markers from the plurality of strip sensors comprises
 detecting the plurality of bio markers from each of the plurality of detection sections.

3. The method of claim 2, wherein the recognizing of the plurality of strip sensors comprises:
 determining whether the plurality of strip sensors are detected by a camera, and
 if the plurality of strip sensors is detected, arraying a focus of the camera for the plurality of strip sensors.

4. The method of claim 2, wherein the detecting of the plurality of bio markers from each of the plurality of detection sections comprises:
 computing a representative value of a third measurement value in the detection section,
 standardizing the computed representative value of the third measurement value in the detection section based on a reference color set for each of the plurality of bio markers, converting the standardized representative value of the third measurement value into a concentration of at least one of the plurality of bio markers,
applying each of the plurality of preset weights to each of the plurality of converted bio marker concentrations, respectively, and
displaying the weight-applied bio marker concentrations.

5. The method of claim 1, wherein the displaying, based on the computed representative value, of the request for re-inserting the at least one of the plurality of strip sensors comprises
if the computed representative value of the first measurement value in the determination section is not less than a preset first measurement value, displaying the request for re-inserting the at least one of the plurality of strip sensors.

6. The method of claim 5, wherein the identifying of the determination section in each of the plurality of strip sensors comprises:
identifying a plurality of particular sections where the first measurement value in each of the plurality of strip sensors is not more than a preset second measurement value, and
identifying a particular section having a larger measurement value among the plurality of identified particular sections as the determination section.

7. The method of claim 1, wherein the identifying of the plurality of detection sections in each of the plurality of strip sensors comprises:
detecting a second measurement value for each of the plurality of strip sensors,
identifying a plurality of particular sections where the detected second measurement value for each of the plurality of strip sensors is not more than a preset second measurement value, and
identifying a detection section among the plurality of identified particular sections according to a predetermined condition.

8. The method of claim 7, wherein the identifying of the detection section among the plurality of identified particular sections according to the predetermined condition comprises:
identifying a particular section having a larger measurement value among the identified particular sections as the determination section,
if a distance between a particular section having a smaller measurement value among the identified particular sections and the identified determination section is not less than a predetermined distance, identifying a particular section spaced apart from the determination section at the predetermined distance as the detection section, and
if the distance between the particular section having the smaller measurement value among the identified particular sections and the identified determination section is not more than the predetermined distance, identifying the particular section having the smaller measurement value as the detection section.

9. An electronic device for generating health information from a plurality of strip sensors, the electronic device comprising:
a camera sensor configured to detect a plurality of bio markers from the plurality of strip sensors, wherein the camera sensor is configured to detect the plurality of bio markers includes recognizing the plurality of strip sensors and identify a plurality of detection sections in each of the plurality of strip sensors;

a processor configured to generate user health information based on the detected plurality of bio markers; and
a display configured to display the generated user health information
wherein the processor is further configured to:
identify a determination section in each of the plurality of strip sensors,
compute a representative value of a first measurement value in the identified determination section, and
control the display based on the computed representative value to display a request for re-inserting at least one of the plurality of strip sensors.

10. The electronic device of claim 9, wherein the camera sensor is configured to
detect the plurality of bio markers from each of the plurality of detection sections.

11. The electronic device of claim 10,
wherein the processor is further configured to determine whether the plurality of strip sensors is detected by a camera, and
wherein if the plurality of strip sensors is detected, focus the camera for the plurality of strip sensors.

12. The electronic device of claim 10, wherein the processor is further configured to:
compute a representative value of a third measurement value in the detection section,
standardize the computed representative value of the third measurement value in the detection section based on a reference color set for each of the plurality of bio markers,
convert the standardized representative value of the third measurement value into a concentration of the bio marker,
apply each of the plurality of preset weights to each of the plurality of converted bio marker concentrations, respectively, and
display the weight-applied bio marker concentrations.

13. The electronic device of claim 9, wherein the processor is further configured to
if the computed representative value of the first measurement value in the determination section is not less than a preset first measurement value, display the request for re-inserting the strip sensor.

14. The electronic device of claim 13, wherein the processor is further configured to:
identify a plurality of particular sections where the first measurement value in each strip sensor is not more than a preset second measurement value, and
identify a particular section having a larger measurement value among the plurality of identified particular sections as the determination section.

15. The electronic device of claim 9, wherein the processor is further configured to:
detect a second measurement value for each of the plurality of strip sensors,
identify a plurality of particular sections where the detected second measurement value in each strip sensor is not more than a preset second measurement value, and
identify a detection section among the plurality of identified particular sections according to a predetermined condition.

16. The electronic device of claim 15, wherein the processor is further configured to
identify a particular section having a larger measurement value among the identified particular sections as the determination section, if a distance between a particular section having a smaller measurement value among the identified particular sections and the identified determination section is not less than a predetermined distance, identify a particular section spaced apart from the determination section at the predetermined distance as the detection section, and if the distance between the particular section having the smaller measurement value among the identified particular sections and the identified determination section is not more than the predetermined distance, identify the particular section having the smaller measurement value as the detection section.

\* \* \* \* \*